(12) United States Patent
Solomon

(10) Patent No.: US 11,745,181 B2
(45) Date of Patent: Sep. 5, 2023

(54) DEVICES AND METHODS FOR BIOASSAY

(71) Applicant: Unchained Labs, Pleasanton, CA (US)

(72) Inventor: Deepak Solomon, San Diego, CA (US)

(73) Assignee: UNCHAINED LABS, Pleasanton, CA (US)

( * ) Notice: Subject to any disclaimer, the term of this patent is extended or adjusted under 35 U.S.C. 154(b) by 554 days.

(21) Appl. No.: 16/637,406

(22) PCT Filed: Aug. 8, 2018

(86) PCT No.: PCT/US2018/045793
§ 371 (c)(1),
(2) Date: Feb. 7, 2020

(87) PCT Pub. No.: WO2019/032690
PCT Pub. Date: Feb. 14, 2019

(65) Prior Publication Data
US 2020/0179930 A1 Jun. 11, 2020

Related U.S. Application Data

(60) Provisional application No. 62/543,324, filed on Aug. 9, 2017.

(51) Int. Cl.
*B01L 3/00* (2006.01)
*G01N 33/50* (2006.01)

(52) U.S. Cl.
CPC ... *B01L 3/502761* (2013.01); *B01L 3/502738* (2013.01); *G01N 33/5044* (2013.01);
(Continued)

(58) Field of Classification Search
CPC ....... B01L 2200/028; B01L 2200/0647; B01L 2200/0668; B01L 2200/16;
(Continued)

(56) References Cited

U.S. PATENT DOCUMENTS 723,826 A 3/1903 Buysse
5,932,418 A 8/1999 Yager
(Continued)

FOREIGN PATENT DOCUMENTS

AU 2013204820 B2 1/2014
CA 2521862 A1 10/2004
(Continued)

OTHER PUBLICATIONS

Extended European Search Report dated Jul. 28, 2021, for EP Application No. 18 844 318.8. filed on Aug. 8, 2018, 12 pages,.
(Continued)

*Primary Examiner* — Lyle Alexander
*Assistant Examiner* — Jonathan Bortoli
(74) *Attorney, Agent, or Firm* — COOLEY LLP

(57) ABSTRACT

This disclosure provides fluidic devices and methods for performing a bioassay, for example bioassays performed on zebrafish. The disclosure provides various fluidic devices for performing a bioassay that include a sample chamber in fluid communication with an air valve; and a bioassay channel that can include a first bioassay region, for example for studying zebrafish in early stages of development and a second bioassay region, for studying zebrafish in later stages of development. The first bioassay region and second bioassay region can be defined using pillars, such as a first and second array of pillars. The fluidic device can have additional structures that are provided herein. Also provided herein are sample loading manifold devices for loading zebrafish embryos into fluidic devices and reagent delivery manifold devices for delivering reagents to fluidic devices. Furthermore, methods using any or all of the devices are provided.

18 Claims, 7 Drawing Sheets

(52) U.S. Cl.
CPC ... *B01L 2200/0647* (2013.01); *B01L 2200/16* (2013.01); *B01L 2300/041* (2013.01); *B01L 2300/06* (2013.01); *B01L 2300/0816* (2013.01); *B01L 2300/0883* (2013.01); *B01L 2300/12* (2013.01); *B01L 2300/168* (2013.01); *B01L 2400/06* (2013.01)

(58) Field of Classification Search
CPC .......... B01L 2300/041; B01L 2300/06; B01L 2300/0816; B01L 2300/0883; B01L 2300/12; B01L 2300/168; B01L 2400/06; B01L 2400/086; B01L 3/502738; B01L 3/502746; B01L 3/502761; G01N 2333/4603; G01N 33/5044; G01N 33/5088
See application file for complete search history.

(56) References Cited

U.S. PATENT DOCUMENTS

| | | | |
|---|---|---|---|
| 6,048,734 | A | 4/2000 | Burns et al. |
| 6,293,012 | B1 | 9/2001 | Moles |
| 6,319,469 | B1 | 11/2001 | Mian et al. |
| 7,708,949 | B2 | 5/2010 | Stone et al. |
| 8,592,221 | B2 | 11/2013 | Fraden et al. |
| 8,765,485 | B2 | 7/2014 | Link et al. |
| 9,315,768 | B2 | 4/2016 | Vrouwe et al. |
| 10,875,017 | B2 | 12/2020 | Solomon et al. |
| 10,981,166 | B2 | 4/2021 | Solomon |
| 11,305,279 | B2 | 4/2022 | Solomon |
| 2002/0033193 | A1 | 3/2002 | McNeely et al. |
| 2002/0036018 | A1 | 3/2002 | McNeely et al. |
| 2002/0075363 | A1 | 6/2002 | McNeely et al. |
| 2002/0097633 | A1 | 7/2002 | O'Connor |
| 2003/0138829 | A1 | 7/2003 | Unger et al. |
| 2003/0159999 | A1 | 8/2003 | Oakey et al. |
| 2004/0072278 | A1 | 4/2004 | Chou et al. |
| 2004/0137607 | A1 | 7/2004 | Tanaami et al. |
| 2004/0206408 | A1 | 10/2004 | Peters et al. |
| 2006/0018790 | A1 | 1/2006 | Naka et al. |
| 2007/0037199 | A1 | 2/2007 | Takahashi et al. |
| 2007/0110631 | A1 | 5/2007 | Ajdari |
| 2007/0125942 | A1 | 6/2007 | Kido |
| 2007/0195127 | A1 | 8/2007 | Ahn et al. |
| 2008/0233607 | A1 | 9/2008 | Yu et al. |
| 2009/0136982 | A1 | 5/2009 | Tang et al. |
| 2009/0151792 | A1 | 6/2009 | Noda |
| 2010/0165784 | A1 | 7/2010 | Jovanovich et al. |
| 2010/0221831 | A1 | 9/2010 | Miyazaki et al. |
| 2010/0252118 | A1 | 10/2010 | Fraden et al. |
| 2011/0256574 | A1* | 10/2011 | Zhang ............... C12M 23/16 435/325 |
| 2011/0269226 | A1 | 11/2011 | Van Noort et al. |
| 2011/0301058 | A1 | 12/2011 | Cheng et al. |
| 2012/0219947 | A1 | 8/2012 | Yurkovetsky |
| 2012/0244043 | A1 | 9/2012 | LeBlanc et al. |
| 2013/0136694 | A1 | 5/2013 | Martinho et al. |
| 2013/0236376 | A1 | 9/2013 | Augstein et al. |
| 2013/0280131 | A1 | 10/2013 | Handique et al. |
| 2013/0337578 | A1 | 12/2013 | Delamarche et al. |
| 2014/0051062 | A1 | 2/2014 | Vanapalli et al. |
| 2014/0246098 | A1 | 9/2014 | Fraden et al. |
| 2014/0302160 | A1 | 10/2014 | Achrol et al. |
| 2014/0377850 | A1 | 12/2014 | Handique et al. |
| 2015/0044688 | A1 | 2/2015 | Richter et al. |
| 2015/0125947 | A1 | 5/2015 | Korczyk et al. |
| 2015/0184127 | A1 | 7/2015 | White et al. |
| 2016/0214104 | A1 | 7/2016 | Schwemmer et al. |
| 2016/0332163 | A1 | 11/2016 | Wang et al. |
| 2016/0361715 | A1* | 12/2016 | Shi .................... B01L 3/50273 |
| 2016/0361716 | A1 | 12/2016 | Solomon |
| 2017/0232440 | A1 | 8/2017 | Ismagilov et al. |
| 2018/0071735 | A1 | 3/2018 | Linder et al. |
| 2019/0054467 | A1 | 2/2019 | Handique |
| 2020/0055051 | A1 | 2/2020 | Solomon et al. |
| 2020/0261910 | A1 | 8/2020 | Solomon |
| 2021/0114022 | A1 | 4/2021 | Solomon et al. |
| 2022/0266212 | A1 | 8/2022 | Solomon |

FOREIGN PATENT DOCUMENTS

| | | |
|---|---|---|
| EP | 2364774 A2 | 9/2011 |
| EP | 3615220 A1 | 3/2020 |
| FR | 2897282 A1 | 8/2007 |
| JP | 2000515630 A | 11/2000 |
| JP | 2004163104 A | 6/2004 |
| WO | WO-2006/052223 A1 | 5/2006 |
| WO | WO-2006096571 A2 | 9/2006 |
| WO | WO-2008097559 A2 | 8/2008 |
| WO | WO-2008130623 A1 | 10/2008 |
| WO | WO-2010111231 A1 | 9/2010 |
| WO | WO-2012154688 A2 | 11/2012 |
| WO | WO-2016118949 A1 | 7/2016 |
| WO | WO-2016187561 A1 | 11/2016 |
| WO | WO-2016/201163 A1 | 12/2016 |
| WO | WO-2016201430 A1 | 12/2016 |
| WO | WO-2017/027838 A1 | 2/2017 |
| WO | WO-2017180949 A1 | 10/2017 |
| WO | WO-2018200896 A1 | 11/2018 |
| WO | WO-2019032690 A1 | 2/2019 |
| WO | WO-2019094775 A1 | 5/2019 |
| WO | WO-2020087032 A2 | 4/2020 |
| WO | WO-2021067353 A1 | 4/2021 |
| WO | WO-2022146770 A1 | 7/2022 |
| WO | WO-2023023492 A1 | 2/2023 |

OTHER PUBLICATIONS

International Search Report dated Oct. 23, 2018, for PCT Application No. PCT/US2018/045793, filed on Aug. 8, 2018, 2 pages.
Partial Supplementary European Search Report dated Apr. 21, 2021, for EP Application No. 18 844 318.8, filed on Aug. 8, 2018, 12 pages.
Written Opinion of the International Searching Authority dated Oct. 23, 2018, for PCT Application No. PCT/US2018/045793, filed on Aug. 8, 2018, 10 pages.
Clausell-Tormos, et al., "An Automated Two-phase Microfluidic System for Kinetic Analyses and the Screening of Compound Libraries," Lab on a Chip, 2010, Issue 10, pp. 1302-1307.
Communication pursuant to Article 94(3) EPC for European Patent Application No. 16 740 896.2 dated May 9, 2019. 4 pages.
Communication pursuant to Article 94(3) EPC for European Patent Application No. 16 740 896.2 dated Sep. 21, 2020. 4 pages.
Communication pursuant to Article 94(3) EPC for European Patent Application No. 18206472.5 dated Jan. 7, 2020. 5 pages.
Communication pursuant to Article 94(3) EPC for European Patent Application No. 18206472.5 dated Sep. 16, 2020, 5 pages.
Extended European Search Report for European Patent Application No. 16 74 0896, dated Jun. 6, 2018. 8 pages.
Extended European Search Report for European Patent Application No. 16808519.9, dated Nov. 12, 2018. 9 pages.
Extended European Search Report for European Patent Application No. 18206472.5, dated Jan. 22, 2019. 9 pages.
Extended European Search Report dated Dec. 1, 2020, for EP Application No. 18791954.3, filed on Apr. 27, 2018, 7 pages.
Extended European Search Report dated Oct. 10, 2022, for EP Application No. 19876942.4, filed on Oct. 25, 2019, 9 pages.
Extended European Search Report dated Oct. 5, 2021 for EP Application No. 18876268.6, filed Nov. 9, 2018, 9 pages.
Final Rejection dated Dec. 12, 2019, from U.S. Appl. No. 15/005,341, 34 pages.
Final Rejection dated Feb. 4, 2019, from U.S. Appl. No. 15/005,341, 42 pages.
International Application No. PCT/US2018/060104, International Search Report dated Feb. 28, 2019, 14 pages.
International Search Report and Written Opinion for International Application No. PCT/US2022/074985 dated Jan. 6, 2023, 14 pages.

(56) References Cited

OTHER PUBLICATIONS

International Application No. PCT/US2018/029692, International Search Report dated Jul. 12, 2018, 4 pages.
International Search Report and Written Opinion dated Sep. 1, 2016 for PCT Application No. PCT/US2016/037225 filed Jun. 13, 2016. 5 pages.
International Search Report and Written Opinion dated Jan. 15, 2020, for PCT Application No. PCT/US2019/058202, 8 pages.
International Search Report and Written Opinion dated Jun. 15, 2022, for PCT Application No. PCT/US2021/064512, filed on Dec. 21, 2021, 19 pages.
International Search Report and Written Opinion of the International Searching Authority dated Jul. 12, 2018, for PCT Application No. PCT/US2018/029692, 22 pages.
International Search Report dated Jun. 2, 2016 for PCT/US16/14704. 18 pages.
Non-Final Rejection dated Jun. 3, 2019, from U.S. Appl. No. 15/005,341, 33 pages.
Non-Final Rejection dated Mar. 9, 2018, from U.S. Appl. No. 15/005,341, 15 pages.
Notice of Allowance dated Aug. 21, 2020, from U.S. Appl. No. 15/005,341, 36 pages.
Notice of Allowance dated Dec. 4, 2020, from U.S. Appl. No. 15/005,341, 7 pages.
Resto, Pedro J. et al., "High Speed Droplet-based Delivery System for Passive Pumping in Microfluidic Devices", Sep. 2, 2009, Journal of Visual Experiments, Issue 31, p. 1-5. (Year: 2009).
Written Opinion dated Jun. 2, 2016, for PCT Application No. PCT/US2016/014704, filed on Jan. 25, 2016, 8 pages.
Xiaowen Huang et al., "On-Site Formation of Emulsions by Controlled Air Plugs", Small, vol. 10, No. 4, Feb. 1, 2014 (Feb. 1, 2014), pp. 758-765.
Zhu and Wang, "Passive and active droplet generation with Microfluidics: a review" Lab Chip (2017) 17:34-75.

\* cited by examiner

DEVICES AND METHODS FOR BIOASSAY

RELATED APPLICATIONS

This application claims the benefit of U.S. Ser. No. 62/543,324 entitled "DEVICES AND METHODS FOR BIOASSAY" filed on Aug. 9, 2017, which is incorporated herein by reference in its entirety.

FIELD OF THE DISCLOSURE

This disclosure is generally related to fluidics devices and methods for performing a bioassay.

BACKGROUND

Zebrafish (Donio *rerio*) has emerged as one of the most powerful, robust, and relevant small animal models for drug discovery and development over the last decade. Zebrafish has become an attractive model for bioassay, for example in drug screening and discovery, due to the greater than 70% match between the zebrafish and human genome, and because it provides a whole-organism, vertebrate model. Additionally, the high reproduction rate, ease of genetic manipulation, ease of culture, size and optically transparency make an attractive animal model for numerous fields of research and development. As such, there has been a large drive both from academia and industry to make it a widely-accepted model.

Current methodologies for zebrafish screening are complex, time and labor intensive, as well as fraught with difficulty in the manipulation of zebrafish embryos and larvae. For example, immobilization of zebrafish in a biologically-compatible matrix, such as agar, agarose, or methylcellulose for analysis and imaging is not only time consuming, but requires that an embryo or larva be prepared in a matrix while in it is in liquid state before gelation. There is a narrow temperature range for maintaining a liquid state for such matrices that may not be compatible with a living organism, such as a zebrafish embryo or larva. As such, the manipulation to fix zebrafish embryos and larvae in various gel matrices is known to result in damage to such organisms. As an alternative, anesthetizing zebrafish embryos and larvae, for example with tricaine, is also currently widely adopted as part of an immobilization technique. However, given the nature of biological variation, effective dosing can be problematic. Additionally, for example, results of a drug screening assay, especially one that includes analysis of brain function, may be affected by anesthesia and produce different results than those performed on non-anesthetized embryos or larvae.

Accordingly, there is a need in the art to provide academic and industrial laboratories with devices and methods that streamline the workflow for various studies using zebrafish as a biological model, as well as preserving the biological integrity of the organism over the course of time defined by various experimental protocols.

SUMMARY OF THE DISCLOSURE

This disclosure provides fluidic devices and methods for performing a bioassay. Such bioassays, in illustrative embodiments are performed on zebrafish, including zebrafish embryos and larvae. In one aspect, provided herein is a fluidic device for bioassay, or for performing a bioassay that includes a fluidic chamber that includes:

a sample chamber, which in illustrative embodiments is in fluid communication with an air valve; and a bioassay channel, wherein the bioassay channel has a first end in fluid communication with the sample chamber and in illustrative embodiments a second end in fluid communication with a first outlet chamber. In some embodiments, the bioassay chamber can include a first and second array of pillars that allow fluid flow around each pillar and through the bioassay channel, but are configured to position a zebrafish embryo and/or larvae. In some embodiments, the bioassay chamber can have a first bioassay region in fluid communication with the sample chamber and a second bioassay region in fluid communication with the first outlet chamber. These embodiments can be combined such that the first and second array of pillars are configured to define the first and the second bioassay regions of the bioassay channel. The fluidic device can have additional structures that are provided herein.

Further provided herein is a sample loading manifold device and a reagent delivery manifold device that can be configured and positioned to work with the fluidic device for performing a bioassay. Additionally, provided herein are methods that can use the fluidic device for performing a bioassay, as well as optionally the sample loading manifold device and the reagent delivery manifold device. Details regarding various and illustrative embodiments of such devices are provided herein.

Other embodiments are also contemplated, as will be understood by those of ordinary skill in the art from this disclosure. Furthermore, details regarding aspects and embodiments of the present disclosure are provided throughout this patent application. Sections and section headers are not intended to limit combinations of methods, compositions, and kits or functional elements therein.

BRIEF DESCRIPTION OF THE DRAWINGS

A better understanding of the features and advantages of the present disclosure will be obtained by reference to the accompanying drawings, which are each intended to illustrate various embodiments of the present teachings, not limit, the present teachings.

In FIG. 6, 601 is a first port of a first fluid transport channel 601A; 602 is a second port of a second fluid transport channel 602A; 603 is a downstream fluid transport channel connected to both fluid transport channels 601A and 602A; 604 is a circular design feature (a "window") allowing for user visualization of volume ratios between fluids from port 601 and port 602; 605 is a serpentine mixing channel that promotes fluid mixing between fluids from port 601 and port 602; 100 is a fluidic device for example as detailed in FIG. 2A connected in series and in fluidic communication downstream of serpentine mixing channel 605 by a post-mixing channel 606.

DETAILED DESCRIPTION OF THE DISCLOSURE

The present inventors have innovated fluidic devices and methods that can efficiently load, align, and manipulate zebrafish embryos and larvae, as well as provide for detection and analysis throughout the entire duration of an experimental protocol. Such devices and methods of the present teachings provide in various aspects, at least one of the following: (a) biologically-compatible and efficient loading of zebrafish embryos into a fluidic device of the present teachings; (b) on-device chorion removal; (c) continuous alignment of embryos and larvae in the same focal plane for continuous high-quality imaging; (d) ease of culture of zebrafish larvae for up to 10 days post fertilization with on-device food and media replenishment, and (e) biologically-compatible on-device physical containment and positioning of zebrafish embryos and larvae for continuous drug perfusion studies, thereby precluding the use of harsh immobilization techniques during the course of running an experimental protocol.

Figure 1:
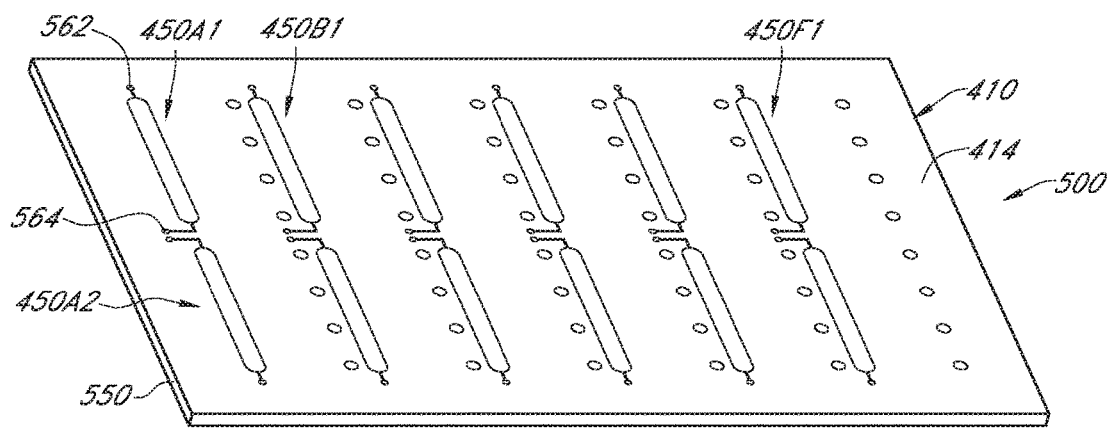
FIG. 1 is an exploded isometric perspective view of various devices for the manipulation and analysis of zebrafish embryos and larvae.
Figure 1:
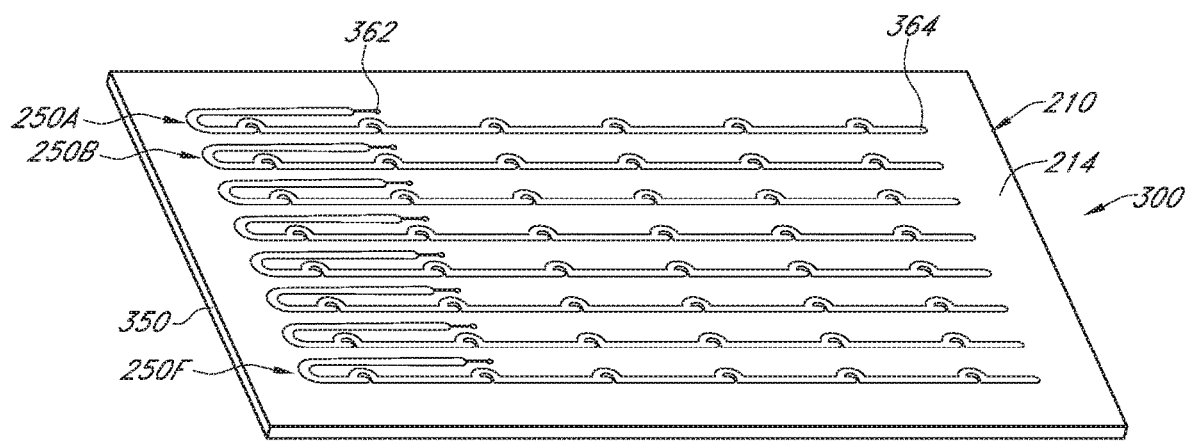
Figure 1:
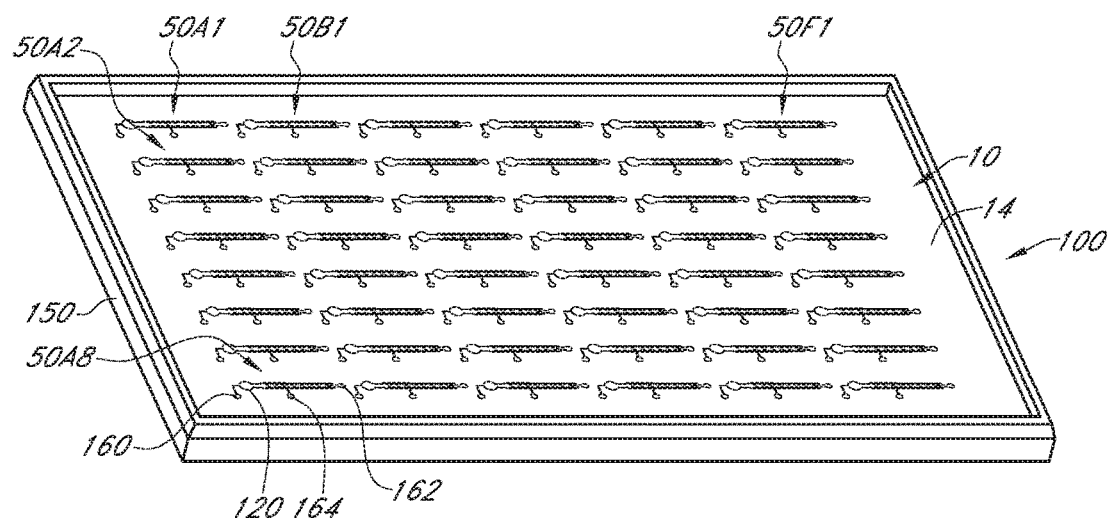

FIG. 1 depicts fluidic device 100, which is an exploded isometric view of a fluidic device/assembly of the present teachings. As an overview to FIG. 1, various embodiments of fluidic device 100 can be used for the manipulation and analysis of zebrafish embryos and larvae. In addition to a fluidic device 100, sample loading manifold 300 can be used for loading zebrafish embryos into fluidic device 100. As such, the manifold 300 is operable to load zebrafish into fluidic device 100. Reagent loading manifold 500 can be used for delivering, for example, various biological agents during a drug screening bioassay, or delivering or replenishing media. As such, the reagent manifold 500 is operable to deliver reagents to fluidic device 100.

Fluidic device 100 can be fabricated using, for example, but not limited to, various soft lithographic micro-embossing techniques. In various embodiments of fluidic device 100 of FIG. 1, one or more of a fluidic chamber, such as fluidic chamber 50A1 of fluidic device 100, can be fabricated in a substrate. In various embodiments, substrate 10 can be an optically transmissive polymer, providing good optical transmission from, for example at least about 85% to 90% optical transmission over a wavelength range of about 400 nm to about 800 nm. Examples of polymeric materials having good optical transmission properties for the fabrication of fluidic device 100 using a variety of fabrication methods matched to substrate material properties include organosilicon polymers, such as polydimethylsiloxane (PDMS), cyclic-olefin polymers (COP), cydic-olefin copolymers (COC), polystyrene polymers, polycarbonate polymers, and acrylate polymers.

Fluidic chambers, such as fluidic chambers 50A1, can be patterned in various arrangements, such as a linear or 2-dimensional array. As depicted in FIG. 1, fluidic chambers are depicted in a 2-dimensional array defined by rows, such as a row defined by 50A1 through 50F1, and a column, such as a column defined by 50A1 through 50A8. Such arrays may be useful for integration with other formats well-known in biological testing, such as various microtiter plate formats, though any arrangement of fluidic chambers on a substrate for any type of experimental protocol. Substrate 10 can have a first surface on which the fluidic chambers are fabricated that can be mounted to an optically transmissive cover plate 150, which can readily enable optical detection. Optically transmissive cover plate 150 can have at least the same optical transmission as substrate 10; at least about 85% to 90%, and in certain embodiments 80% to 90%, 85% to 90%, 80% to 95%, 90% to 95%, 85% to 95%, 85% to 98%, or 85% to 99% over a wavelength range of between about 400 nm to about 800 nm, or between 400 nm to 800 nm. Cover plate 150 can be selected from a variety of glass materials, such as a glass slide, or can be a polymeric material, such as any of the exemplary polymeric materials suitable for substrate 10, and in illustrative embodiments is an optically clear polymer. The cover plate 150 in illustrative embodiments, is typically positioned at the bottom of the fluidic device 100 and can serve to hold fluid inside the chambers and channels of the fluidic device 100 for designs where the fluidic channels would otherwise be open to air. The entire fluidic device 100 in illustrative embodiments can be flipped during use and imaged from the top, which would result in the cover plate 150 being the top of the fluidic device 100.

Figure 2A:
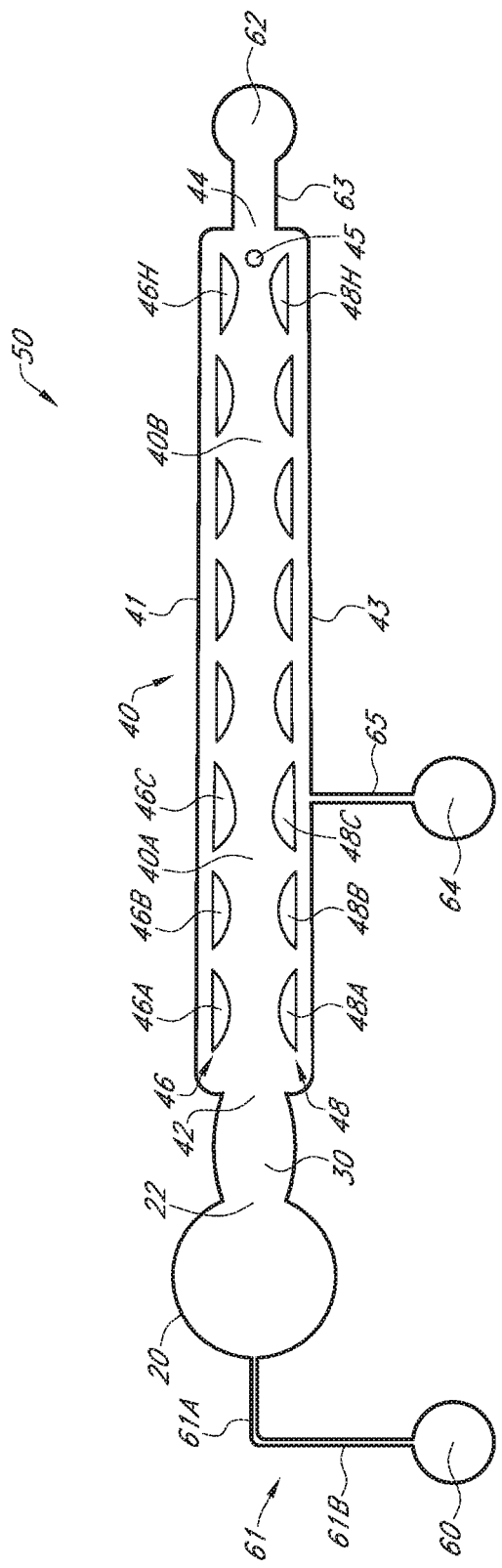
FIG. 2A is a top schematic view of a fluidic chamber of a fluidic device for the manipulation and analysis of zebrafish embryos and larvae.
Figure 2B:
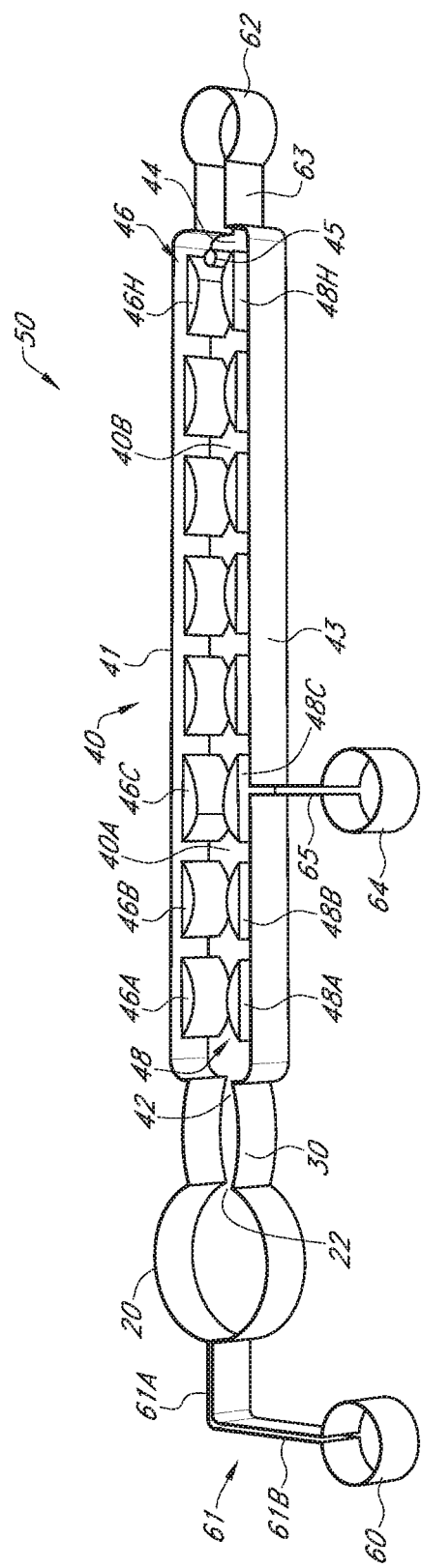
FIG. 2B is an isometric view of FIG. 2A.

Second substrate surface 14, opposing the first substrate surface on which the fluidic chambers are formed, can have a variety of ports fabricated through the body of the substrate to provide external fluid communication to various substructures of a fluidic chamber of the present teachings, such as depicted for representative fluidic chamber 50A8 of FIG. 1, and representative fluidic chamber 50 of FIGS. 2A and 2B. For example, first fluidic device port 160 of FIG. 1 can provide external fluid communication to air valve 60 of fluidic chamber 50, depicted in FIG. 2. In illustrative embodiments, the air valve 60 is a passive air valve. Moreover, sample loading can be done in manual or automated mode by delivery of a zebrafish embryo to sample chamber 20 of fluidic chamber 50 of FIG. 2 through second fluidic device port 120 depicted in FIG. 1. Finally, various reagents can be delivered or withdrawn through third fluidic device port 162 in fluid communication with first outlet chamber 62, as well as through forth fluidic device port 164 in fluid communication with second outlet chamber 64. In illustrative embodiments, the device is a millifluidic device. The substrate thickness for illustrative embodiments of fluidic device 100 of the present teachings can be about 1 mm (millimeter)+/−30%, or +/−20%, so that the thickness of the polymeric substrate for illustrative embodiments of fluidic device 100 of FIG. 1 can be from 800μ (microns) to 1200μ (microns). In certain illustrative embodiments of fluidic device 100 of the present teachings, a polymeric substrate can be about 1 mm (millimeter)+/−40% or +/−30%. The thickness of the polymeric substrate for illustrative embodiments of fluidic device 100 of FIG. 1 can be from 700μ (microns) to 1300μ (microns).

FIG. 2A is a top schematic view of fluidic chamber 50 that can be used for the manipulation of zebrafish embryos and larvae over a period of time of embryonic and larval development, which can be from about 4, 5, or 12 hours post fertilization, or 1 day or 2 days post fertilization (dpf) to early-stage larval development, which can be about 1, 2, 3, 4, or 5 dpf, through late-stage larval development, which can be about 6, 7, 8, 9, or 10 dpf. FIG. 2B is an isometric perspective view of fluidic chamber 50 of FIG. 2A, and provides an additional perspective of features of fluidic chamber 50. As such, all disclosure herein given in reference to FIG. 2A is equally applicable to FIG. 28. In illustrative embodiments, the fluidic channel holds a volume of 5-25 ul or for example, 10-15 ul.

According to the present disclosure, various embodiments of fluidic chamber 50 of FIG. 2A can include sample chamber 20, which is dimensioned for receiving a zebrafish embryo. For example, certain embodiments of sample chamber 20 can have a diameter of 2 mm +/−0.4 mm or in illustrative embodiments +/−0.2 mm, and a depth, which is the depth across bioassay channel 40, of 0.60 mm +/−0.2 mm in certain embodiments and +/−0.1 mm in illustrative embodiments. A zebrafish embryo encased in the protective chorion is about 1.5 mm +/−0.3 mm in diameter. In that regard, sample chamber is dimensioned to receive the range of expected sizes for a zebrafish embryo. Sample chamber 20 is in fluid communication with air valve 60 via air vent channel 61. Air valve 60 is dimensioned to provide hydrodynamic balance across fluidic chamber 50. Air vent channel 61 has first segment 61A and second segment 618, which is depicted in FIG. 2A in a non-limiting example as orthogonal to first channel segment 61A. The length and dimension of air vent channel 61 are selected to prevent liquid flow from sample chamber 20 from occurring into the air vent channel 61. In comparison to the dimensions given for sample chamber 20, the total channel length of air vent channel 61, in certain embodiments is 3 mm +/−0.2 mm and in illustrative embodiments is 3 mm +/−0.1 mm, having a channel width of 80µ (micron)+/−0.2 um or in illustrative embodiments +/−0.1 um, while air valve 60 can be, for example, 1 mm in diameter +/−0.2 mm or in illustrative embodiments +/−0.1 mm. These dimensions in this illustrative embodiment ensure that air valve 60 and air vent channel 61 are gas-filled during use of bioassay channel 40. Additionally, as was previously disclosed herein, air valve, which can also referred be referred to as gas vent or air vent 60 is in fluid communication with the external environment through port 160 (FIG. 1), so that air valve 60 is at external pressure.

Sample chamber 20 can be proximal to processing chamber 30, and in fluid communication with processing chamber 30 at sample chamber opening 22. Processing chamber 30 can have a diverging geometry in illustrative examples, as illustrated in FIGS. 2A and 2B. Accordingly, in illustrative embodiments as shown in FIGS. 2A and 2B the processing chamber 30 has rounded walls that are wider in the center of the processing chamber 30 than at the opening at its ends. Processing chamber 30 can be used for on-device removal of a chorion of a zebrafish embryo. Recalling, the chorion is a protective membrane surrounding a zebrafish embryo, and can act as a substantial barrier to, for example, drug diffusion across the chorion. As such, it is desirable to remove the chorion in order to perform various bioassays.

Accordingly provided herein in one aspect, is a method (and a fluidic device for performing such method, having the device features listed below for such method) for removing the chorion from a zebrafish embryo using a fluidic device that includes the following steps:

loading a zebrafish embryo surrounded by a chorion into a sample chamber of a fluidic device;

exposing the zebrafish embryo surrounded by the chorion within the sample chamber to a chorion-weakening chemical or agent under effective conditions to weaken the chorion or incubating the zebrafish embryo in the sample chamber until dechorionation of the zebrafish embryo naturally takes place (for example after 2 to 4 days post fertilization or in illustrative embodiments 3 days post fertilization); and forcing the zebrafish embryo surrounded by the weakened chorion through a processing chamber that connects the sample chamber to a bioassay channel, wherein the processing chamber has a geometry that is effective for removing a weakened chorion surrounding an embryo. For example, in illustrative embodiments, the processing chamber has a diverging geometry (i.e. larger in the center than at the ends) and preferably rounded walls, with dimensions that are smaller than the largest dimension of the chorion when surrounding an embryo, but larger than the largest dimension of the zebrafish embryo. In illustrative embodiments, the processing chamber has an elongated geometry that is larger in the center than at the ends and is between 750µ (micron)+/−10% or +/−5% and 1000µ(micron)+/−10% or +/−5% in width at its widest region, which in these embodiments is a central region. In certain embodiments, as illustrated in FIGS. 2A and 2B, a processing chamber can have a diverging geometry. A zebrafish embryo encased in the protective chorion is about 1.5 mm +/−0.3 mm in diameter, and post dechorionation the embryo is about 0.5 mm. In comparison, processing chamber in the illustrative embodiment shown in FIGS. 2A and 2B can have a width at both the sample chamber opening 22 and bioassay channel first end or inlet 42 of 0.75 mm +/−0.15 mm, +/−0.10 mm or +/−0.05 mm and a compartment length of 1.4 mm +/−0.15 mm, +/−0.10 mm or +/−0.05 mm.

Various chorion-weakening chemicals or agents are known in the art and can be used in the devices and methods provided herein. For example, in illustrative embodiments, the chorion-weakening chemical or agent is a protease or a mixture of proteases, and in illustrative embodiments, is Pronase (Sigma Aldrich). Accordingly, in illustrative embodiments the chorion-weaking chemical is a mixture of several nonspecific endo- and exoproteases that under specified conditions can completely digest proteins. For example, the mixture of proteases can be a mixture of proteases isolated from the extracellular fluid of *Streptomyces griseus*. In the present teachings, the concentration and time are defined to weaken the chorion without harming the embryo. With respect to embryo development, the time for performing the on-chip chorion removal can be any time after 5 hours post-fertilization and before hatching, and for example in illustrative embodiments can be done at 5-24, 6-15, 8-14 or 10-12 hours post fertilization. A skilled artisan will understand that effective conditions can be determined by varying the concentration of the chorion-weakening agent (e.g. protease or mixtures of proteases) under various temperatures and times. For example, Pronase, or a similar mixture of proteases with composition and activity similar to Pronase, for example as sold by Sigma Aldrich on the filing date of the present invention, can be used at a concentration of between 1 and 5 mg/ml for between 5 and 15 minutes. The chorion-weakening chemical is typically in a buffered media that is otherwise safe for the zebrafish embryo, such as E3 media.

As a non-limiting example referring again to FIGS. 2A and 2B, an on-chip method for removal of the chorion can be performed by adding 10 µl of a solution of Pronase at a concentration of 1.25 mg/ml to an embryo in sample chamber 20, and then aspirating 10 µl from first outlet chamber 62 to effectively expose the embryo to the Pronase solution. In this illustrative example, after incubation of the embryo with the Pronase solution for 5 minutes, the Pronase solution can be flushed from sample chamber 20 by pipetting 10 µp of media into sample chamber 20 and then drawing the media through fluidic chamber 50 by aspirating 10µ of media from first outlet chamber 62. This can be followed by repeated flushing of fluidic chamber 50 as previously disclosed until the embryo is pulled through the processing chamber 30, thereby stripping the chorion from around the embryo. Once passing through the processing chamber 30, the embryo is then positioned in bioassay channel 40.

In Illustrative embodiments of the present teachings, bioassay channel 40 can be in flow communication with processing chamber 30 and with first outlet chamber 62. As depicted in FIG. 2A, bioassay channel 40 can have first end or inlet 42 proximal to processing chamber 30 and second end 44, which is typically downstream from the first end or inlet 42 and is proximal to first outlet chamber 62, the distance between the two which defines the length of bioassay channel 40. In illustrative embodiments of fluidic chamber 50, the length of bioassay channel 40 can be 10.2 mm +/−0.2 mm or +/−0.1 mm. Bioassay channel 40 is also defined by first lateral wall 41 and opposing second lateral wall 43, which also define the overall channel width of bioassay channel 40. In illustrative embodiments of fluidic chamber 50, the overall width of bioassay channel 40 can be 1.4 mm +/−0.15 mm, +/−0.10 mm, or +/−0.05 mm.

Proximal to first lateral wall 41 is first pillar array 46, and proximal to second lateral wall 43 is second pillar array 48. As depicted in FIG. 2A, each pillar array is comprised of a pillar structure, such as pillar structure 46A through pillar structure 46H of first pillar array 46, and such as pillar structure 48A through pillar structure 48H of second pillar array 48. At second end 44 of bioassay channel 40, channel post 45 is located. In illustrative examples, the first and opposing second set of pillar arrays define an effective channel width for containing and positioning a zebrafish embryo or larva. Further, first pillar array 46, second pillar array 48 and channel post 45 are structural elements that can physically contain and position a zebrafish embryo or larva without the need for being physically embedded in a gel media or without the use of an anesthetic. The curvilinear shape of each pillar structure facing the channel ensures that a zebrafish embryo or larva will contact a smooth surface to prevent injury. The spacing between the pillars and between the pillar arrays and the lateral walls of bioassay channel 40 create a fluid cushion around a zebrafish embryo or larva when no fluid is actively being drawn through the channel, as well as an even flow of fluid around zebrafish embryo or larva when fluid is drawn through the channel.

Accordingly, in one aspect, provided herein is a method for positioning a zebrafish embryo within a fluidic device, wherein the method includes the following steps:
loading the zebrafish embryo into a fluidic chamber of the fluidic device, wherein the fluidic chamber comprises a bioassay channel comprising a first and second array of pillars configured to position the zebrafish embryo between the first and opposing second array of pillars; and incubating the zebrafish embryo within the fluidic chamber such that the zebrafish embryo is positioned between the first and opposing second array of pillars, thereby mounting the zebrafish embryo. The second array of pillars is typically configured such that it is opposing the first array of pillars, as provided herein in illustrative fluidic devices as for example depicted in FIGS. 2A and 2B.

Moreover, the present inventors have recognized that regions in bioassay channel 40 that can selectively contain and selectively position a zebrafish in various stages of development of bioassay channel 40 can be designed by varying the spacing between the pillars, the shape and size of opposing sets of pillar structures, as well as the position of opposing sets of pillar structures from the lateral wall of bioassay channel 40. For example, variation in the effective channel width of bioassay channel 40 can define regions in bioassay channel 40 that can contain and position a zebrafish in various stages of development of bioassay channel 40, such as first bioassay channel region 40A and second bioassay channel region 408. As previously described herein, a zebrafish embryo post removal of the chorion, a protective membrane that surrounds embryo, is about 0.5 mm (millimeters). Further, in the early stage of development, which is between 3-5 days post fertilization (dpf), a zebrafish with yolk sack will require more space than for a zebrafish in late stage of development, which is up to between 6-10 days dpf. As such, variation in physiology and morphology of the subject organism over the duration of an experimental protocol can change substantially. Furthermore, it is contemplated within the present disclosure that a zebrafish embryo can be removed from the device, such as by reversing flow through the device and removing the zebrafish through the sample loading chamber, without damaging the zebrafish, and incubated with feeding outside the device, such as in a Petri dish, for up to 3 weeks post fertilization, and then inserted back into the device through the sample chamber, for further visual analysis within the bioassay channel.

In illustrative embodiments provided herein, fluidic chambers and particularly bioassay regions of such chambers can be configured to accommodate morphological changes during zebrafish development. Accordingly, provided herein in one aspect is a method for mounting, positioning, and/or analyzing a zebrafish embryo (and a fluidic device for performing such method, having the device features listed below in such method), that includes the following steps:

loading the zebrafish embryo into a sample chamber of a fluidic chamber of a fluidic device, wherein the fluidic chamber comprises a bioassay channel comprising a first bioassay region and a second bioassay region;

creating a flow within the fluidic chamber to move the zebrafish embryo into the first bioassay region;

incubating the zebrafish embryo within the first bioassay region until it is up to 5 days post-fertilization and such that it develops into a zebrafish larva; and creating a flow within the fluidic chamber to move the zebrafish larva into the second bioassay region, wherein the zebrafish larva is between 4-5 days post-fertilization when it is moved to the second bioassay region. In certain aspects, the method is performed without anaesthetizing the zebrafish embryo or larva. In certain embodiment, a zebrafish larva is in the second bioassay region if it is 6 days post-fertilization to 10 days post-fertilization.

FIG. 2A provides an illustrative embodiment with respect to pillar orientation and structure within a bioassay channel 40 of a fluidic chamber 50. In that regard, in illustrative embodiments of fluidic chamber 50, pillar structure 46A and opposing pillar structure 48A can define an effective channel width of 0.60 mm +/−0.06 mm as measured between the narrowest distance between the structures. Additionally, the distance between the backside of pillar structure 46A and opposing pillar structure 48A from lateral wall 41 and lateral wall 43 in certain illustrative embodiments, is 200µ (micron)+/−20µ (micron). The distance between the backside of pillar structure 468 and opposing pillar structure 488 from lateral wall 41 and lateral wall 43, respectively, in certain illustrative embodiments, is 230µ (micron)+/−25µ (micron), so that the effective bioassay channel width between pillar structure 468 and opposing pillar structure 488 is narrower in that part of the bioassay channel in certain illustrative embodiments having a width of 0.550 mm +/−0.05 mm as measured between the narrowest distance between the structures. For pillar structure 46C and opposing pillar structure 48C, the distance between the backside of pillar structure 46C and opposing pillar structure 48C from lateral wall 41 and lateral wall 43, respectively, in certain illustrative embodiments, is 250μ (micron)+/−25μ (micron). However, as depicted in FIG. 2A, the shape and size of this set of opposing pillars can be altered so that in certain illustrative embodiments of fluidic chamber 50 of the present teachings, the effective bioassay channel width between pillar structure 46C and opposing pillar structure 48C is 0.43 mm +/−0.04 mm as measured between the narrowest distance between the structures. The widest opening of the channel proximal to the processing chamber ensures that an embryo can be received into bioassay channel 40, while the narrowing of the channel by pillar structure 46C and opposing pillar structure 48C ensures that an embryonic or early-stage zebrafish will be contained in bioassay region 40A. Accordingly, the variation of the shape and size of opposing sets of pillar structures, as well as the position of opposing sets of pillar structures from the lateral wall of bioassay channel 40, can define first bioassay channel region 40A for selectively containing and positioning embryonic or early-stage zebrafish.

Similarly, varying of the shape and size of opposing sets of pillar structures, as well as the position of opposing sets of pillar structures from the lateral wall define second bioassay channel region 408 of FIG. 2A for selectively containing and positioning late-stage zebrafish. As the yolk sack is adsorbed by a developing zebrafish larva, its overall size diminishes, so that at about 6 dpf, a zebrafish larva can pass through the effective channel width defined by pillar structure 46C and opposing pillar structure 48C For various embodiments of fluidic chamber 50 of the present teachings, the effective channel width defined by pillars (also called pillar structures herein) 46D through 46G proximal to lateral wall 41 and opposing pillars 480 through 48G proximal to lateral wall 43 in certain illustrative embodiments can define an effective channel width of 0.45 mm +/−0.04 mm, while the distance between pillar 46H and opposing 48H in certain illustrative embodiments can be 0.370 mm +/−0.04 mm. The distance between the backside of pillar structures 460 through 46G and opposing pillar structures 48D through 486 from lateral wall 41 and lateral wall 43, respectively, in certain illustrative embodiments is 250μ (micron)+/−25μ (micron). In comparison, the distance between the backside of pillar structure 46H and opposing pillar structure 48H from lateral wall 41 and lateral wall 43, respectively, in certain illustrative embodiments is 350μ (micron) +/−35μ (micron). Additionally, the size and shape of pillar structure 46H and opposing pillar structure 48H can be altered as well. In that regard, the narrowing of the channel by pillar 46H and opposing 48H, in conjunction with channel post 45 can ensure that a late-stage zebrafish larva will be contained in bioassay region 408.

Further, the lateral spacing of pillars in pillar arrays of various embodiments of bioassay channel design can be set to specifically orient and position a zebrafish. For example, the length of longest dimension for each pillar as depicted in FIG. 2A can be, in certain illustrative examples, 1.0 mm +/−0.1 mm, while the distance between each pillar can be, in certain illustrative examples, 0.250 mm +/−0.03 mm. This pillar configuration can generally orient a zebrafish in a lateral orientation with respect to the field of view through of an optically transmissive cover plate, such as cover plate 150 of FIG. 1. Repeated flushing of media through bioassay channel 40 can effectively reorient a zebrafish to a desired orientation for viewing while performing a bioassay. According to the present teachings, adjustment of pillar shape, number and size, as well as adjustment of the distance between pillar structures can be done to selectively provide a lateral, dorsal or ventral orientation with respect to the field of view. In exemplary embodiments, a set of pillars that in illustrative embodiments forms an array of pillars can include, and in illustrative embodiments a linear array of opposing pillars According to the present disclosure, in illustrative embodiments of fluidic chamber 50, first outlet chamber 62 can be 1.00 mm +/−0.20 mm, +/−0.15 mm, or +/−0.10 mm in diameter, while first outlet chamber channel 63 can have a channel width of 0.5 mm +/−0.10 mm or +/−0.05 mm, and a channel length of about 0.82 mm +/−0.16 mm or +/−0.08 mm. First outlet chamber 62 can be used for ready removal and replenishment of fluids in fluidic chamber 50, such as media or other reagents. In a similar fashion, second outlet chamber 64 can be used for removal and replenishment of fluids. Given the position of second outlet chamber 64 at the end of bioassay channel region 40A, it can be used for removal and replenishment of fluids in bioassay channel region 40A, for experimental protocols designed to study early-stage zebrafish. This can be accomplished in certain examples, by closing first outlet chamber 62 while having second outlet chamber 64 in an open position. In illustrative embodiments of fluidic chamber 50, second outlet chamber 64 can be 1.00 mm +/−0.2 mm or +/−0.1 mm in diameter, while second outlet chamber channel 65 can have a channel width of 0.1 mm +/−0.02 mm or +/−0.01 mm. The dimensions of second outlet chamber channel 65 provide that fluids will flow through bioassay channel 40, when drawn from sample chamber 20 to first outlet chamber 62.

Finally, in discussing features of fluidic chamber 50, it should be noted that in illustrative fluidic devices of the present teaching, such as fluidic device 100 of FIG. 1, an optically transmissive cover plate, such as cover plate 150 of FIG. 1, can enable continuous visualization of fluidic device 100, which can include a plurality of fluidic chambers, such as fluidic chamber 50 of FIG. 2A. In that regard, visualization of fluidic device of the present teachings can be done over the duration of an experimental protocol from the deposition of an embryo in sample chamber 20, through passage of an embryo through processing chamber 30, and throughout the duration of a zebrafish bioassay in bioassay channel 40.

Accordingly, provided herein in one aspect is a method (and a fluidic device for performing such method, having the device features listed below in such method) for analyzing a zebrafish embryo and/or larva, that includes the following steps:

loading a zebrafish embryo into a sample chamber of a fluidic chamber of a fluidic device, wherein the fluidic chamber comprises a bioassay channel comprising a first bioassay region and a second bioassay region;

creating a flow within the fluidic chamber to move the zebrafish embryo into the first bioassay region;

incubating the zebrafish embryo within the first bioassay region until it is up to 5 days post-fertilization and such that it develops into a zebrafish larva; and creating a flow within the fluidic chamber to move the zebrafish larva into the second bioassay region, wherein the zebrafish larva is between 4-5 days post-fertilization when it is moved to the second bioassay region, wherein the zebrafish embryo and/or the zebrafish larva is visualized.

In certain embodiments, the visualization can be visualization and/or imaging at any time point or continuously as the zebrafish develops in the fluidic chamber. In certain embodiments, the zebrafish can be visualized and/or imaged using a microscope or such visualization and/or imaging can be performed with a CCD camera. In particularly illustrative embodiments, the first and second bioassay regions include a first and second array of pillars as disclosed herein, and the zebrafish embryo and/or the zebrafish larva is visualized or imaged when it is positioned between the first and second array of pillars. The zebrafish embryo or larva can be in a lateral position, a dorsal position, or a ventral position with respect to the field of visualization of the bioassay channel. Furthermore, the zebrafish embryo can be analyzed such as by visual analysis and/or imaging while it is positioned in the sample chamber, the first bioassay region, and/or the second bioassay region.

Figure 3:
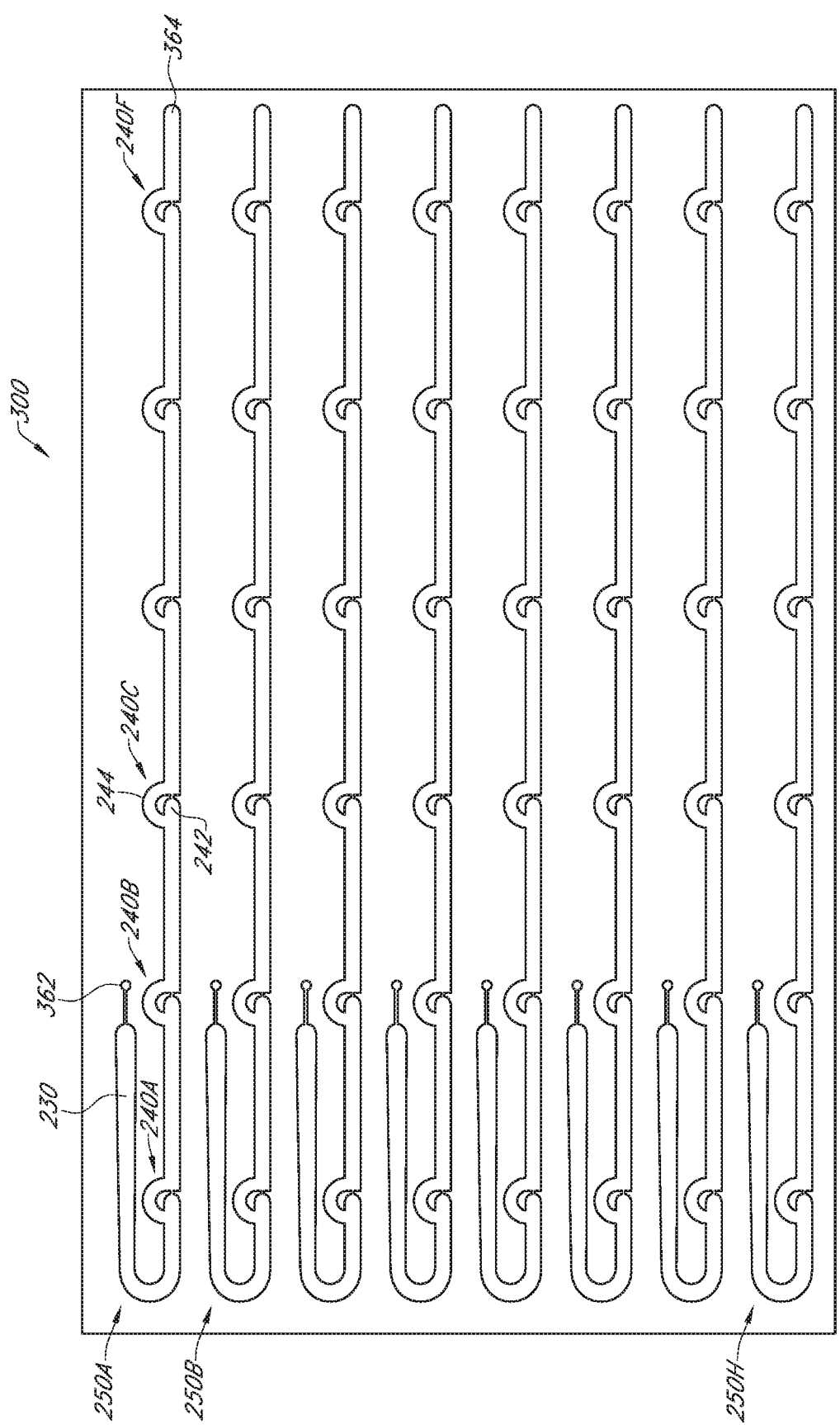
FIG. 3 is top schematic view of a sample loading manifold in accordance to various embodiments of devices and methods of the present teachings.

FIG. 1 depicts sample loading manifold 300 positioned over fluidic device 100. FIG. 3 is a top schematic expanded view of sample loading manifold device 300 according to illustrative embodiments of devices and methods of the present disclosure. Loading manifold can have one or a plurality of a sample loading channel, such as sample loading channel 250A through 250H of FIG. 3. A sample loading channel of the present disclosure can have a sample loading inlet port and a sample loading outlet port, such as sample loading inlet port 362 and sample loading outlet port 364 of sample loading channel 250A as depicted in FIG. 3. A sample loading channel of the present disclosure includes a sample loading chamber proximal to a sample loading inlet port, such as sample loading chamber 230 depicted in FIG. 3 as proximal to a sample loading inlet port 362. In illustrative embodiments, the sample loading chamber 230 has a width that is slightly larger than the sample loading channel 250 so as to improve ease of loading embryos into the sample loading channel 250. For example, in an illustrative embodiment, the width of the sample loading chamber 230 is 2 mm +/−0.20 mm or +/−0.10 mm and the width of the sample loading channel 250, can be 1.5 mm +/−0.20 mm or +/−0.10 mm. The length of loading chamber 230 can be set based on the number of embryos to be loaded. For example, in illustrative embodiments, the length of the loading chamber 230 is 1.5 mm +/−0.30 mm or +/−0.15 mm times the number of embryos to be loaded. For example, the loading chamber 230 can be 9 mm +/−1.8 mm or +/−0.9 mm in order to accommodate 6 embryos. Additionally, a sample loading channel can have one or more of a loading structure in fluid communication with the loading chamber. In FIG. 3, sample loading channel 250A is depicted as having sample loading structures 240A through 240F. Each loading structure can include a sample trap and a sample channel bypass loop. For example, loading structure 240C as depicted includes sample trap 242 and sample channel bypass loop 244. According to the present teachings, a sample trap can be in fluid communication with the sample loading channel, while a sample channel bypass loop can be in fluid communication with the sample trap and the sample loading channel. For various embodiments of a sample loading manifold of the present teachings, when the sample trap is loaded with a zebrafish embryo, fluid flow through the sample loading channel is maintained through the sample channel bypass loop.

Figure 4A:
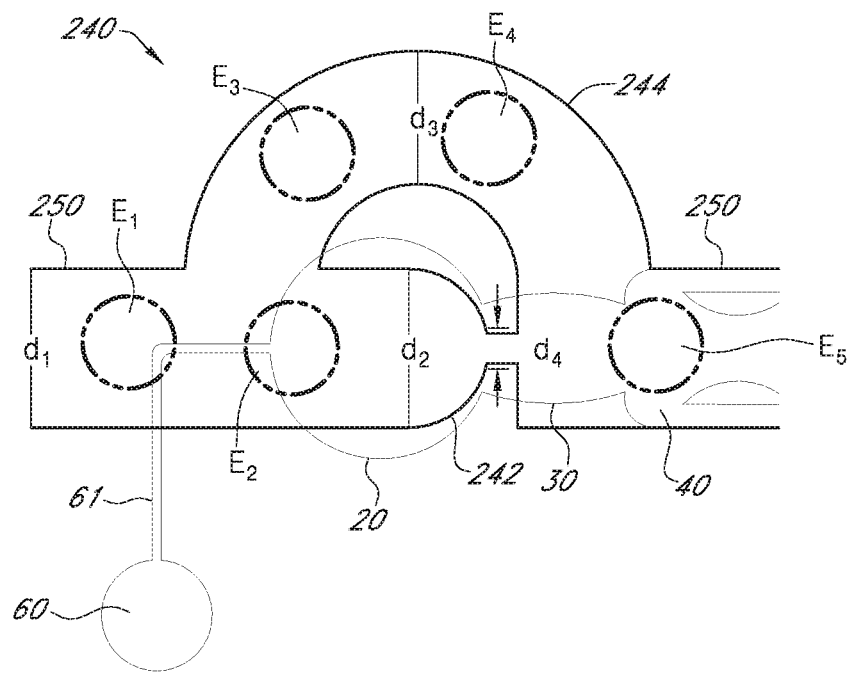
FIGS. 4A and 4B are top schematic expanded views of a portion of a sample loading manifold mounted upon and aligned with a fluidic device, which depict the trapping of zebrafish embryos by a sample loading manifold for ready deposition in a fluidic device of the present teachings.
Figure 4B:
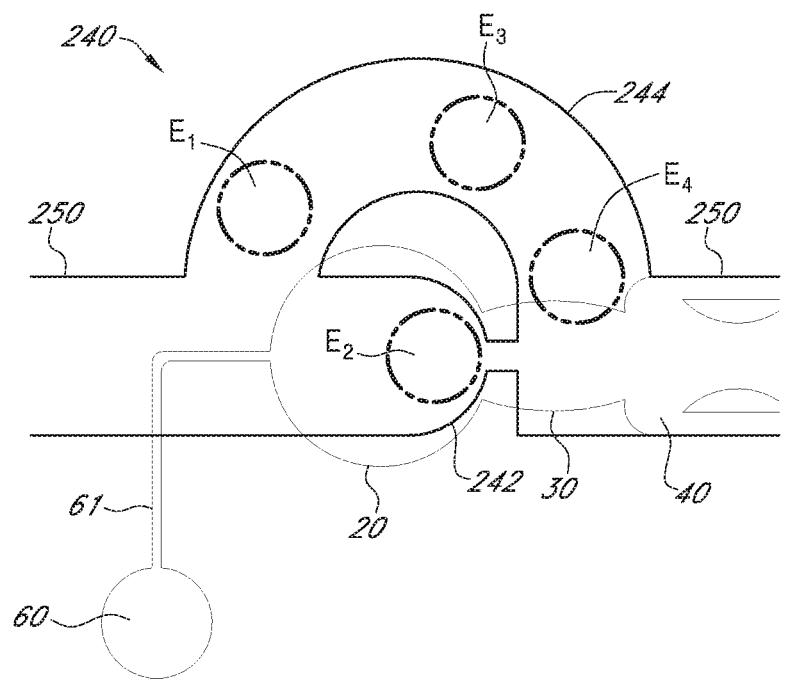

FIGS. 4A and 4B provide cross-sectional views of an illustrative loading structure 240 of an illustrative sample loading manifold device positioned over a portion of an illustrative fluidic chamber of a fluidic device such that the sample trap 242 is aligned over a sample chamber 20. In illustrative embodiments the loading channel 250 has a diameter (d1) of 1.5 mm (+/−0.20 mm or +/−0.10 mm), and the bypass loop 244 is 1.25 mm (+/−0.20 or +/−0.10 mm) in its largest dimension ($d_3$), the trap 242 is 1.5 mm (+/−0.30 or +/−0.15) mm in its largest dimension ($d_2$), and a post-trap channel (up/down arrows) downstream from the trap 242 and formed at a distal end of the trap 242 and connecting the trap to the loading channel 250 at the point where the bypass loop 244 joins back into the loading channel 250 has a width ($d_4$) of 0.3 mm (+/−0.20 or +/−0.10 mm). In this illustrative example, the width of the post-trap channel (up/down arrows) is less than the diameter of a zebrafish embryo and the distal surface of the trap 242 is curved and has an opening that leads to the post-trap channel (up/down arrows) such that when a zebrafish embryo occupies the trap, it reduces or even stops flow through the post-trap channel (up/down arrow) and flow is then redirected through the bypass loop 244.

In some aspects, provided herein is a method for loading a plurality of zebrafish embryos into a plurality of fluidic chambers in a fluidic device, that includes the following steps:

loading the plurality of zebrafish embryos into a loading chamber of a sample loading manifold device, wherein the loading chamber is in fluid communication with a loading channel that is in fluid communication with a plurality of loading structures that comprise a trap and a bypass loop around the trap;

creating a flow such that the plurality of zebrafish embryos move into the loading channel and then into a loading structure, wherein when a zebrafish embryo of the plurality of zebrafish embryos enters a trap within the loading structure, it is held against the distal wall of the trap, thereby reducing or in illustrative embodiments, blocking flow through a post-trap channel connected to the trap through an opening in the distal surface of the trap, such that a next zebrafish embryo approaching the trap is carried around the trap by flow around the trap and through the channel bypass loop to a next loading structure; and reducing or eliminating the flow through the loading channel such that embryos that are held in place in a trap, are carried by gravity or another force into a sample chamber of a fluidic chamber of a fluidic device. In certain illustrative embodiments, the trap has a curved distal surface;

Before use of a sample loading manifold device, before or after it is aligned on top of a fluidic device, fluidic chambers of the fluidic device can be loaded with media (e.g. E3 media). The loading chambers of the sample loading manifold can be covered, such as with tape, and media, such as E3 media, can be flushed through the inlet of the sample loading manifold such that media is deposited inside traps 242 of the loading channel 250.

With further reference again to FIG. 3, any covering over the loading chambers 230 of the sample manifold device 300 can be removed and zebrafish embryos can be deposited (e.g. dropped) into the loading chamber 230, which can be covered again. Media can then be passed through an inlet port (362) of the loading channel to create a flow such that when a sample comprising one or typically a plurality of zebrafish embryos ($E_1$-$E_4$) are loaded into a sample loading chamber 230 they enter a sample loading channel 250 and migrate into a sample loading structure 240.

FIGS. 4A and 4B illustrative loading structure 240 at a first timepoint (shown in FIG. 4A) and a second, later timepoint (shown in FIG. 4B), after zebrafish embryos ($E_1$-$E_5$) migrate into a loading structure 240. When an embryo approaches a trap ($E_2$) it enters the trap 242 if the trap 242 is empty and as shown in FIG. 4B is pressed up against a distal wall of the trap by the flow in the loading channel 250, and is considered deposited in the trap 242, which in illustrative embodiments, stops most or all flow through the post-trap channel (up/down arrows). As shown in FIG. 4B, once the trap 242 is occupied by an embryo ($E_2$) and flow through the post-trap channel (up/down arrows) is reduced or stopped, another embryo ($E_1$) approaching the trap 242 is directed by the flow around the trap 242 through the sample channel bypass loop 244. Embryos that are not deposited in the trap 242 travel around the trap through the sample channel bypass loop 244 then back to the loading channel 250 where they travel to a next loading structure 240 downstream and in fluid communication with the loading channel 250. Thus, the design of the illustrative loading structure 240 in FIGS. 4A and 4B prevents a second embryo from depositing into a trap 242 if there is already an embryo present in the trap 242.

After at least some of the traps 242 are loaded with zebrafish embryos ($E_1$-$E_5$), the embryos travel from the traps 242 into sample loading chambers 20. To help facilitate movement of the embryos (($E_1$-$E_5$) through the loading channel 250 and into a trap 242, in illustrative embodiments, media, such as E3 media for example, can be passed through an inlet port (e.g. 362 in FIG. 3) of the loading channel 250 using a pipette, such as a 1 ml pipette. In illustrative embodiments, a slow and smooth flow is created when adding media through the inlet port (e.g. 362 in FIG. 3). As discussed, the design of the illustrative device in FIGS. 4A and 4B prevents a second embryo from depositing into a trap 242 if there is already an embryo present in the trap 242. The process of adding media into the loading channel 250 can be repeated in order to facilitate depositing more embryos each into more of the traps 242 of a series of traps 242 that are in fluidic communication along a loading channel 250.

Once a sufficient number of traps have a zebrafish embryo deposited therein, a downward force can be created to move the embryos from the trap 242 into a sample chamber 20 aligned with the trap 242. In an illustrative embodiment, the downward force is created by stopping the addition of media into the loading channel 250 and allowing a gravitation force on embryos deposited in traps 242 to then move downward into a sample loading chamber 20 aligned directly under the trap 242. In illustrative embodiments, the top surface and/or the bottom surface of the sample loading manifold device 300 is transparent or at least sufficiently clear to allow visual observation, typically through a microscope, of location and movement of zebrafish embryos within the sample loading manifold device 300. Thus, the movement and depositing of embryos within the sample loading device 300 can be monitored and the process of adding media to the loading channel to create a flow to move the embryos into traps can be repeated until sufficient number of embryos are deposited into traps. For example, media can be added and/or the sample loading manifold device 300 can be otherwise agitated such that at least 25, 50, 75, 90, 95, 99, or 100% of the traps have a single embryo deposited therein. The sample loading manifold 300 can be removed from a position in contact with and typically above a fluidic device 100 after sufficient number of zebrafish embryos have been loaded one each into sample loading chambers of a fluidic device.

Figure 5:
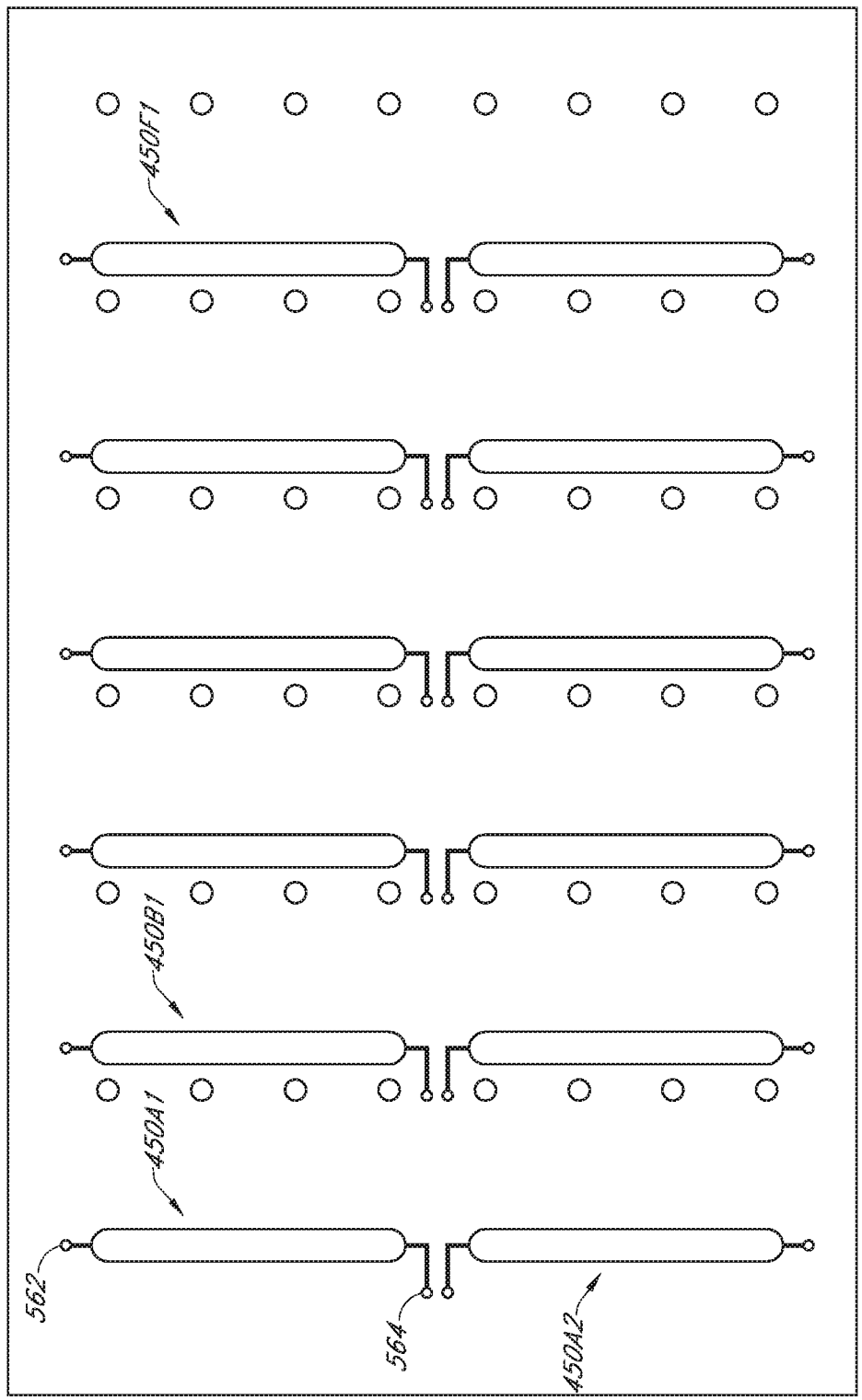
FIG. 5 is a schematic view of a reagent loading manifold in accordance to various embodiments of devices and methods of the present teachings.

FIG. 1 depicts reagent delivery manifold device 500, which can be positioned over fluidic device 100 to facilitate delivery of reagents into the fluidic chambers of the fluidic device 100. FIG. 5 is a top schematic expanded view of reagent delivery manifold device 500 according to certain illustrative embodiments of the present disclosure. Reagent delivery manifold can have one or a plurality of reagent chambers, such as reagent chambers 450A1 through 450F1 of FIG. 5 or a second row of 450A2 through 450F2. Each reagent chamber 450 can have an inlet and outlet such as reagent chamber inlet port 562 and reagent chamber outlet port 564 of the illustrative reagent delivery manifold 500 of FIG. 5. A reagent can be added into a reagent chamber for example by pipetting into the inlet. The reagent delivery manifold device 500 can be positioned over a surface of a fluidic device such that each reagent chamber is positioned and/or aligned over or otherwise in fluidic communication with at least one sample chamber, and typically a plurality of sample chambers of the fluidic device. For example, a reagent chamber can be in fluid communication with, and positioned and aligned over, 2, 3, 4, 5, 6, 7, 8, 9, 10, 11, 12, 18, 24, 48, 72, or 96 sample chambers. Additionally in such embodiments, or in other embodiments, the reagent delivery manifold device 500 can be positioned over a surface of a fluidic device such that each reagent chamber is positioned and/or aligned over or otherwise in fluidic communication with at least one first and/or second port 601 and 602 of a fluid transport channel 601A and 602A of a fluidic mixing component 600.

Thus, a reagent that is added into a reagent chamber flows into the sample chambers in fluid communication therewith. As such, a reagent chamber facilitates transfer of reagents to multiple sample chambers in a single step. In one embodiment, the reagent delivery manifold device 500 is positioned on top of a top surface of a fluidic device 100 and upon or soon after addition of a liquid in to a reagent chamber, the liquid flows into the sample chambers in fluid connection therewith by gravitational force. A skilled artisan will recognize that other methods and devices can be used to add fluids into multiple sample chambers in a single step, and that such steps can be automated.

In illustrative embodiments, a reagent added into a microfluidic device for a screening method provided herein, which can be added using the reagent delivery manifold device 500, is a test compound. A test compound can be virtually any type of potentially biologically active compound as are known in the art. Non-limiting examples include a nucleic acid such as a polynucleotide or an oligonucleotide, either of which can be DNA or RNA, an antisense RNA or an inhibitory RNA molecule, or a peptide nucleic acid (PNA), a polypeptide, a protein, for example an antibody, a carbohydrate, an inorganic molecule, a small organic molecule, a drug candidate, for example from a library of drug candidates, or an approved drug, for example.

Figure 6:
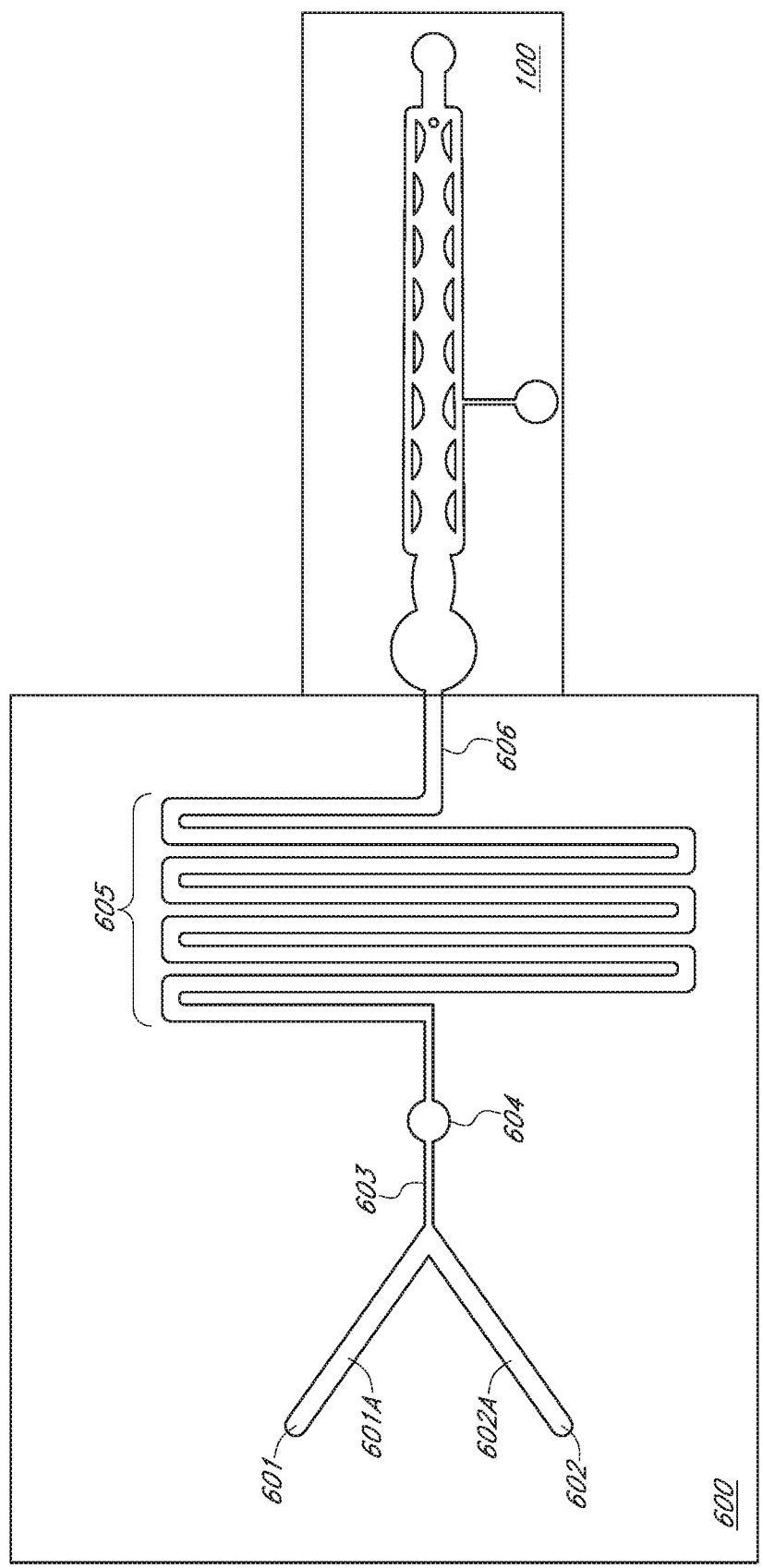
FIG. 6 is a diagram showing a fluidic mixing component 600 coupled in series with a fluidic device 100 as shown in FIG. 2A.

FIG. 6 depicts a fluidic mixing component 600 in fluidic communication with a downstream fluidic device 100, for example as depicted in FIG. 2A. The fluidic mixing component 600 is comprised of parts 601-606, which are in fluidic communication with one another. Before fluid is introduced into the fluidic mixing component 600, the downstream fluidic device 100 can be loaded with a zebrafish embryo or larva as described in the FIG. 2A. After loading of the fluidic device 100 with a zebrafish embryo or larva, or in some embodiments before loading of the zebrafish embryo or larva in the fluidic device 100, the entire fluidic device 100 must be prefilled with fluid by filling from first outlet chamber 62 in FIG. 2A. After the fluidic device 100 has been prefilled, fluid is introduced into the upstream fluidic mixing component 600. Fluid entry can occur in ports 601 or 602, and each respective fluid initially travels through fluid transport channels 601A and 602A. Fluids from the first and second transport channels 601A and 602A converge in the downstream fluid transport channel 603. The initial fluid convergence in the beginning of the downstream fluid transport channel 603 marks the beginning of fluid mixing. The diameter of first and second transport channels 601A and 602A may be the same as, or can be larger (in illustrative embodiments) or smaller than, the downstream fluid transport channel 603. As fluid continues through fluid transport channel 603, in certain illustrative embodiments it reaches a mixing "window" 604, where the interface between fluids can be visualized by the user. The fluid with a higher flow rate will occupy more of this mixing window than the fluid with the lower flow rate, with the ratio of window occupancy being directly related to the flow rate ratio between fluids.

After fluid passes through the fluid transport channel 603 and optional mixing window 604, it reaches a serpentine mixing channel 605. This serpentine channel 605 is designed specifically to ensure thorough fluidic mixing, and in illustrative embodiments, complete fluidic mixing, before fluid moves into the downstream fluidic device 100. Mixing in this serpentine channel 605 relies primarily on diffusion; channel length and channel width are two of the major dimensional factors that influence this diffusion. The channel width and length of the serpentine mixing channel 605 can be chosen to ensure thorough, and in illustrative embodiments complete fluid mixing for the desired fluid input settings. While the serpentine mixing channel 605 in illustrative embodiments is arranged as shown in FIG. 6, in some embodiments the serpentine mixing channel 605 can comprise or be configured in any form other than a straight channel, as long as it creates turbulence and therefore mixing of liquids that pass through it, such as where the serpentine channel 605 comprises one or more complete serpentine coils (e.g., between two to twenty, two to twelve, two to eight, two to six, two to four, four to eight, six to eight, two, five, six, seven, eight, nine, ten, or at least two serpentine coils or turn-backs, alone or combined with straight channels). FIG. 6 shows a serpentine mixing channel with 7 coils or turn-backs.

After the fluid is thoroughly, and in illustrative embodiments completely mixed in the serpentine mixing channel 605, it continues to the fluidic device 100. At this point, incoming fluid will interact with the initial fluid in the serpentine mixing channel 605. Mixed fluid from the fluidic mixing component 600 will flow through and replace the fluid initially loaded in the fluidic device 100 as it travels out of the serpentine mixing channel 605 through the post-mixing channel 606 and into the fluidic device 100.

With respect to dimensions of the fluidic mixing component 600 and its various components, a skilled artisan will understand that various dimensions can be used depending on a particular application. For example, the overall design height of the fluidic mixing component 600 can be equal to the substrate thickness for illustrative embodiments of fluidic device 100 of the present teachings can be from about 100 um to the maximum height of the fluidic device 100 shown in FIG. 2A, and is usually the same height as the features of the fluidic device 100 and constructed in the same substrate 10 as the fluidic device 100. Accordingly, the maximum thickness of the fluidic mixing component 600 can be from 800μ (microns) to 1200μ (microns), 1 mm (millimeter)+/−40% or +/−30%, or 700μ (microns) to 1300μ (microns). In certain non-limiting illustrative embodiments the serpentine mixing channel 605 has a length of approximately 15 to approximately 25 times (e.g., 90.1 mm vs. 4.6 mm in an embodiment of the fluidic mixing component 600 of FIG. 6; e.g., approximately 20 times) the length of the downstream fluid transport channel 603; the serpentine mixing channel 605 and post-mixing channel 606 have similar diameters that are approximately twice the diameter of the downstream fluid transport channel 3; the first and second fluid transport channels 601A and 602A are of approximately the same diameter and length; the length of the downstream fluid transport channel 3 is approximately the same length of the first and second fluid transport channels 601A and 602A; and/or, the diameter of the downstream fluid transport channel 603 is approximately 0.4 the diameter of the first and second fluid transport channels 601A and 602A. However, it is noted that the ratio of the diameter of the downstream fluid transport channel 603 relative to the diameter of the first and second fluid transport channels 601A and 602A is flexible and, e.g., the 0.4 value is only an illustrative ratio.

In certain embodiments, fluidic mixing device parts have the following dimensions, each having a range of +/−25% and in illustrative embodiments +/−10%: the first and second fluid transport channel 601A and 602A each have a width of 500 um and a length of 5340 um; the downstream fluid transport channel 603 has a width of 200 um and a length of 1950 um; the optional mixing window 604 has a radius of 500 um and a circular shape; and the serpentine mixing channel 605 has a width of 500 um and a length of 90 mm, and the post-mixing channel 606 has a width of 500 uM and length of 2 mm; It is noted that, in some embodiments, when differences in diameters are discussed, it is the diameter at the junction of channels being discussed. It is also noted that the diameters of two parts that are in direct fluidic communication with one another will typically be approximately the same unless otherwise noted.

With regards to fluid dispensed in ports 601 or 602, there are a variety of different input parameters. A single port may be used for a single fluid, leaving the other port unused, and the fluidic mixing component 600 may simply serve as a transport channel to the downstream fluidic device 100. Two different fluids may be used, with one fluid having a higher or lower flow rate compared to the other fluid. One fluid may be a concentrated test compound (e.g. drug) solution, while the other fluid may be a buffering solution. By modifying the flow rates of each inputted solution, varying one, two, or more test compound concentrations may be achieved in the mixed solution.

The fluidic mixing component 600 detailed in FIG. 6 allows for dynamic control of solution composition. As mentioned above, this solution may contain a test compound, for example, the concentration of which in solution may need to be adjusted in real time. Multiple input ports and control of input parameters allow for precise control of test compound (or other substance) concentration, and the serpentine mixing channel 605 ensures the test compound (or other substance) is adequately mixed in the desired diluting solution. Independent loading ability of fluidic device 100, combined with the dynamic and real-time solution composition control provided by the fluidic mixing component 600, offers many benefits to the user. In one example, an embryo can be loaded into the sample chamber 20 of the fluidic device 100. A test compound solution of interest can be developed and mixed in the fluidic mixing component 600, the concentration of which is adjustable by the user. Through combination of the fluidic mixing component 600 and the fluidic device 100, constant perfusion drug studies can be performed on the embryo and/or larva through its development, providing a much more tailored and realistic experience than standard static drug studies. The device pictured in FIG. 6 offers a dynamic drug exposure study solution more closely related to in vivo situations than standard static studies.

OTHER ILLUSTRATIVE EMBODIMENTS

This disclosure provides fluidic devices and methods for performing a bioassay. Such bioassays, in illustrative embodiments are performed on zebrafish, including zebrafish embryos and larvae. In one aspect, provided herein is a fluidic device for bioassay, or for performing a bioassay that includes a fluidic chamber that includes a sample chamber in fluid communication with an air valve; and a bioassay channel, wherein the bioassay channel has a first end in fluid communication with the sample chamber and a second end in fluid communication with a first outlet chamber. The sample chamber is typically adapted to receive a zebrafish embryo, which includes, for example, a shape and size as provided in illustrative embodiments herein. Furthermore, the bioassay channel can be configured to position a zebrafish for bioassay.

In some embodiments, the bioassay channel can have a first region and a second region, that are each configured to position a zebrafish, wherein the first region is configured to position a zebrafish during early-stage development and the second region is configured to position a zebrafish during late-stage development.

In some embodiments, the bioassay channel includes pillars, in illustrative embodiments, a first and second array of pillars, that allow fluid flow around each pillar and through the bioassay channel and that are configured to position a zebrafish in the bioassay channel. In illustrative embodiments, the pillars, for example the first and second array of pillars, are configured to position a zebrafish embryo and/or larvae. In some embodiments, the bioassay channel can have a first bioassay region in fluid communication with the sample chamber and a second bioassay region in fluid communication with the first outlet chamber. The first and second array of pillars can be configured to define the first and the second bioassay regions of the bioassay channel. Illustrative embodiments disclosed herein provide detailed sizes and configurations of a first and second array of pillars within a bioassay channel that form a first bioassay region and a second bioassay region.

In some embodiments, a fluidic chamber of a fluidic device provided herein includes a processing chamber positioned between the sample chamber and bioassay channel. The processing chamber in these illustrative embodiments, is adapted to aid in the removal of the chorion of a zebrafish embryo, especially a zebrafish embryo that has a weakened chorion. For example, in an illustrative embodiment, the processing channel has a diverging geometry with dimensions as exemplified herein, that facilitate removal of a chorion. For example, a processing chamber can have a width that is less than the width of a chorion encasing a zebrafish embryo, but larger than the width of a zebrafish embryo. For example, in an illustrative embodiment, the width of processing chamber at both a sample chamber opening and a bioassay channel first end is 0.75 mm +/−0.10 mm or +/−0.05 mm and the processing chamber has a length of 1.4 mm +/−0.10 mm or +/−0.05 mm.

Further provided herein is a sample loading manifold device and a reagent delivery manifold device that can be configured and positioned to work with the fluidic device for performing a bioassay. Additionally, provided herein are methods that can use the fluidic device for performing bioassay, the sample loading manifold device and the reagent delivery manifold device. Details regarding various and illustrative embodiments of such devices are provided herein.

Provided in another aspect herein, a fluidic device comprising:
  a. a sample chamber; and
  b. a bioassay channel, wherein the bioassay channel has a first end in fluid communication with the sample chamber, said bioassay channel comprising a set of pillars configured to position a zebrafish embryo or larva for analysis within the fluidic device.

The fluidic device in the aspect of the preceding paragraph, can be combined with any fluidic device part provided herein, including but not limited to those provided in the above Other Illustrative embodiments or as provided in any aspect or embodiment herein or to perform any of the methods provided herein. For example, in illustrative embodiments, the set of pillars can be configured to position a zebrafish embryo or larva for a bioassay performed by visual analysis, biochemical analysis, or both visual analysis and biochemical analysis. Furthermore, not to be limiting, as an example, the sample chamber can be in fluid communication with an air valve and/or the set of pillars can be configured as a first and opposing second linear array of pillars. Furthermore, the first and second linear array of pillars can be configured to define a first and a second bioassay regions of the bioassay channel, where the first bioassay region is configured to position a zebrafish embryo and the second bioassay region is configured to position a zebrafish larva. In these and other embodiments, the fluidic device further comprises a processing chamber positioned between the sample chamber and the bioassay channel, wherein the processing chamber is a chamber adapted to remove the chorion of a zebrafish embryo especially after it has been weakened through exposure to one or more proteases.

In some embodiments, 1 or more, 2 or more, 1-24, 1-48, 1-96, 1-384, 8-384, 8-192, 8-96, 48-384, 48-192, or 48-384, zebrafish embryos or larvae are present within one or more fluidic devices, for example an array of fluidic devices, provided herein. In illustrative embodiments, the zebrafish embryo or larva is positioned by a set of pillars within a bioassay channel of a fluidic device. The zebrafish embryo or larva can be positioned laterally by the set of pillars, for example where the set of pillars comprises a first and opposing second array of pillars, which can be a first and second linear array of pillars in some embodiments. The set of pillars can include 2, 4, 6, 8, 10, 12, 14, 16, 18, 20, 22, 24, 36, 48, or 96 pillars.

In certain illustrative embodiments, the fluidic device provided herein, such as hereinabove in this section, is in fluidic communication with a fluidic mixing component. The junction between the fluidic mixing component and the sample chamber, in illustrative embodiments, is opposite the end in fluidic communication with a bioassay channel or processing chamber. The fluidic mixing component in illustrative embodiments comprises a serpentine mixing channel that comprises 2 or more, for example 2 to 20, 2 to 12, 2 to 10, 2 to 6 or 2 to 4, 4 to 10, 6 to 8, or 4, 5, 6, 7, 8, 9, or 10 coils or turn-backs.

Provided herein in another aspect, is a fluidic device for removing a chorion from a zebrafish embryo, wherein the device comprises
  a. a sample chamber;
  b. a processing chamber having a first end in fluid communication with the sample chamber, wherein the processing chamber is a chamber adapted to remove the chorion of a zebrafish embryo; and
  c. a bioassay channel, wherein the bioassay channel has a first end in fluid communication with a second end of the processing chamber, wherein the second end of the processing chamber is opposite the first end of the processing chamber, The device for removing a chorion from a zebrafish can include any of the device features provided herein for other device or method aspects. The processing chamber in illustrative embodiments is a chamber adapted to remove the chorion of a zebrafish embryo especially after it has been weakened through exposure to one or more chorion-weakening chemicals or agents under effective conditions to weaken the chorion. Accordingly, the processing chamber has a geometry that is effective for removing a weakened chorion surrounding an embryo. For example, in illustrative embodiments, the processing chamber has a diverging geometry (i.e. larger in the center than at the ends), and in illustrative embodiments, the processing chamber has rounded walls with dimensions that are smaller than the largest dimension of the chorion when surrounding an embryo, but larger than the largest dimension of the zebrafish embryo.

In illustrative embodiments, the processing chamber has an elongated geometry that is larger in the center than at the ends and is between 750 um (micron)+/−10% or +/−5% and 1000 um (micron)+/−10% or +/−5% in width at its widest region. The processing chamber in certain illustrative embodiments has a sample chamber opening where it connects to the sample chamber and connects to the bioassay channel at a bioassay channel first end. In illustrative embodiments, the width at both the sample chamber opening and bioassay channel first end is 0.75 mm +/−0.15 mm, +/−0.10 mm or +/−0.05 mm and a compartment length of 1.4 mm +/−0.15 mm, +/−0.10 mm or +/−0.05 mm.

Provided herein, in other aspects are methods for analyzing zebrafish, typically a plurality of zebrafish embryos and/or larvae, using a fluidic device. Such fluidic devices are typically those disclosed herein as separate aspects. The analysis can include for example, positioning, mounting, dechorionizing and/or visualizing a zebrafish embryo or zebrafish larva developed therefrom, typically a plurality of such zebrafish embryos and/or zebrafish larvae, and can optionally include exposing the zebrafish embryo and/or zebrafish larva to a biological agent.

For example, in one aspect, provided herein is a method for positioning a zebrafish embryo within a fluidic device, wherein the method includes loading the zebrafish embryo into a fluidic chamber of the fluidic device, wherein the fluidic chamber comprises a bioassay channel comprising a first and second array of pillars configured to position the zebrafish embryo between the first and opposing second array of pillars; and incubating the zebrafish embryo within the fluidic chamber such that the zebrafish embryo is positioned between the first and opposing second array of pillars, thereby mounting the zebrafish embryo. The second array of pillars is typically configured such that it is opposing the first array of pillars, as provided herein in fluidic device aspects. In illustrative embodiments, the first and second array of pillars found in the bioassay channel, can have any of the sizes and shapes disclosed herein as part of fluidic device aspects. In an illustrative embodiment, the fluidic device used in the method is a fluidic device according to FIG. 1 herein.

In certain methods herein, a fluidic mixing component is in fluidic communication with a fluidic device used to perform the method. The fluidic mixing component, for example comprising a serpentine mixing channel, can be used to prepare a dilution of a test compound, for example, or to mix 2 or more test compounds, before inputting the test compound(s) into the fluidic device comprising one or more, for example a plurality of zebrafish embryos or larvae. In certain embodiments, the concentration of the test compound is adjusted in real time. Accordingly in certain methods a test compound solution of interest can be developed and mixed in the fluidic mixing component to a target concentration, and the target concentration can be adjusted by the user in real-time as it is input into a fluidic device comprising one or more (e.g. a plurality of) zebrafish embryo or larva. Such methods can provide for example, constant or continuous perfusion drug studies. The zebrafish embryos in some embodiments, have their chorion removed before they are exposed to the test compound.

Other embodiments of the methods and devices provided herein are also contemplated by this disclosure, as would be understood by those of ordinary skill in the art after reading this disclosure including the illustrative embodiments provided herein. Please note that for any aspect or embodiment provided herein with an element that is configured to perform a function, that element is operable to perform such function.

Unless otherwise indicated, the terms and phrases used herein are to be understood as the same would be understood by one of ordinary skill in the art. For instance, terms and phrases used herein can be used consistent with the definition provided by a standard dictionary such as, for example, the Tenth Edition of Merriam Webster's Collegiate Dictionary (1997). The terms "about", "approximately", and the like, when preceding a list of numerical values or range, refer to each individual value in the list or range independently as if each individual value in the list or range was immediately preceded by that term. The values to which the same refer are exactly, close to, or similar thereto (e.g., within about one to about 10 percent of one another). Ranges can be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

Certain embodiments are further disclosed in the following example. This embodiment is provided as an example only and is not intended to limit the scope of the claims in any way.

EXAMPLE

Example 1. Analysis of Zebrafish Using an Illustrative Millifluidic Device for Performing a Bioassay In this example, green fluorescent zebrafish embryos were loaded into the fluidic chambers of μZMount, a non-limiting exemplary fluidic device with the structure provided in FIGS. 1-2 herein and dimensions that were within 5% of the target dimensions as provided herein with reference to the illustrative embodiment provided in FIGS. 1-2, and that includes a plurality of fluidic chambers having the features and within 5% of the target dimensions provided herein for the illustrative embodiment of FIGS. 2A-2B. Various activities of the μZMount were evaluated, including removing the zebrafish chorions using a processing chamber within the fluidic chamber, continuous alignment of the imaging system, media replenishment, and exposing the zebrafish embryos to a biological agent, which in this example was the anti-angiogenic drug SU-5416. These zebrafish were Tg(fli1:EGFP) and expressed enhanced GFP under the control of the fli1 promoter such that the entire vasculature fluoresces. The zebrafish embryos and larvae that developed therefrom, were visualized with high-resolution fluorescent microscopy.

Preparing the μZMount

The cover plate and sample loading manifold device were removed from the top of the device. Surfaces of the device was cleaned by repeatedly attaching and detaching a piece of scotch tape to remove any dust particles. Cleaning was performed, in part, to remove small particles that can prevent the manifold from binding to the device and can prevent a good seal between a sample loading or reagent (e.g. biological agent) delivery manifold and the device.

Loading Zebrafish Embryos

The fluidic device, which also can be referred to as a cultivation device, was filled by carefully pipetting E3 media (5.0 mM NaCl, 0.17 mM KCl, 0.33 mM CaCl, 0.33 mM $MgSO_4$, (pH 7.4) and 0.00001% methylene blue as a fungicide) into the first outlet chambers until media reached the surfaces of the sample chambers. After the fluidic device was filled, a sample loading manifold device was aligned with the fluidic device. The sample loading manifold device included a plurality of loading channels each having a loading chamber proximal to an inlet and a plurality of loading structures in fluid communication with the loading chamber and positioned along the loading channel as shown for the illustrative embodiment in FIG. 3. Each loading structure had a trap and channel bypass loop as shown for the illustrative embodiment in FIGS. 3-4. The sample loading manifold was aligned with the fluidic device so that the loading channels of the sample loading manifold overlaid the fluidic device and the traps of the sample loading manifold overlaid sample chambers of the fluidic device. The loading chambers of the sample manifold device were covered with scotch tape and E3 media was flushed through the inlet of the loading channel using a pipette such that the media was deposited inside the traps of the loading channel.

The scotch tape covering the loading chambers was removed. Green fluorescent Zebrafish embryos (Tg(fli1: EGFP)) were dropped into the loading chambers and the loading chambers were covered with scotch tape again. E3 media was passed through the inlet of the loading channel using a 1 mL pipette with a slow and smooth flow such that the embryos flowed through the channels and dropped into the traps. The presence of embryos in every trap was confirmed visually through a microscope and the process of passing E3 media through the inlet of the loading channel was repeated as necessary. The design of the device prevents a second embryo from depositing into a trap if there is already an embryo present in the trap. After the presence of an embryo in every trap was confirmed, the flow of media into the loading channel was stopped such that flow within the loading channel slowed and gravitational force moved the zebrafish embryos into sample loading chambers aligned below the traps. After all traps had an embryo, the loading manifold was removed and the embryos remained in the sample chambers.

Embryos were dechorionated using the on-device method as discussed below. Alternatively, embryos can be allowed to naturally dechorionate during an extended incubation in the sample chamber of the fluidic device until they naturally dechorionate (about 3 days post fertilization).

Chorion Removal and Mounting

To remove the chorion using the fluidic device, 10 μl of 1.25 mg/ml Pronase in E3 media was added to each of the sample chambers and 10 μl was aspirated from each of the first outlet chambers of the device. This displaced virtually all of the fluids within the fluidic chamber. The embryos were incubated for 5-15 minutes at room temperature to weaken the chorion. The sample chambers were then flushed by adding 10 μl E3 media to each of the sample chambers and aspirating 10 μl from each of the first outlet chambers. This step was repeated for each sample chamber until the embryo was forced into the adjacent first bioassay region by passing it through a bioassay channel first end which effectuated removal of the chorion. Then, the surface of the fluidic device was cleaned with a Kimwipe and then scotch tape as above.

Media Replenishment

A reagent delivery manifold with a general structure similar to FIG. 5 was aligned with the fluidic device and the first outlet chambers of the reagent delivery manifold were covered with scotch tape. Each of the reagent chambers of the reagent delivery manifold was filled with approximately 10 μl E3 media per cultivation chamber in fluid communication through reagent chamber inlet ports. For example, the reagent delivery manifold in FIG. 5 is in fluid communication with 4 cultivation chambers and thus would be filled with approximately 40 μl E3 media. The scotch tape was removed from the first outlet chambers and 10 μl was aspirated therefrom.

Drug Treatment

While the dechorionated embryos were in the first bioassay region, they were treated with 0.1 μM, 1 μM, or 5 μM SU-5416 or 0.1% DMSO as a control for various amounts of time. Each different drug treatment was replenished every 24 hours, effectively dosing the zebrafish at 24, 48, 72, and 96 hours post initial drug treatment. The drug was added in a manner similar to replenishing the media. At 4 dpf, each larvae was moved into its respective second bioassay region by adding 10 μl of media to the sample chamber and aspirated out quickly from the first outlet. The yolk of the zebrafish at this age has depleted enough to allow the fish to flow into the second bioassay region.

Heart Rate Measurement

Heart rate was measured for no less than five embryos per treatment at 48 hours post fertilization (hpf) and 96 hpf. Of the heart rates measured, three of them were recorded using video image capturing techniques for future evaluation. The heart rates were measured by visually inspecting the heart beat and counting the number of beats in 15 seconds and then multiplying by 4.

Survival Rates

Survival rates were determined every 24 hours using morphological changes to characterize whether the embryo or larvae was dead. The embryo or larvae was also visualized for a noticeable heart rate, and if a heart rate was non-existent, then the zebrafish was deemed dead.

Imaging

Embryos were imaged at various time points while within the fluidic device, up to 5 dpf, using high-resolution fluorescence-microscopy. Imaging was performed on the embryos while they were in the sample chambers, the processing chamber, the first bioassay region, and the second bioassay region.

Results

The heart rates (beats/min) of zebrafish treated with 0.1% DMSO or 0.1 μM, 1 μM, or 5 μM SU-5416 for 48 or 96 hours were measured and were within the normal range based on published literature. Furthermore, the control zebrafish showed healthy and stress-free development as there were no signs of deformations. The survival rates of zebrafish at 48, 72, and 96 hours for the zebrafish treated with 1 μM or 5 μM SU-5416 were lower than the zebrafish treated with 0.1% DMSO or 0.1 μM SU-5416.

To show the device's drug screening potential, we challenged the zebrafish larvae with an anti-angiogenic drug, SU-5416. Drug-mediated inhibition of intersegmental and subintestinal vessels sprouting was recorded using high-resolution fluorescence-microscopy. We investigated the effects of SU-5416 and found suppression of angiogenic development similar to published work, as well as concentration dependent dorsalization.

This example demonstrates the potential of fluidic devices provided herein, exemplified by the μZMount, as a screening platform for zebrafish that allows for embryos to be loaded automatically into each well, dechorionated efficiently on-device with no manual interventions, cultured within the device for up to 5 days, and continuously analyzed microscopically from loading of an embryo into the fluidic device through all time points within the device.

The disclosed embodiments, examples and experiments are not intended to limit the scope of the disclosure or to represent that the experiments below are all or the only experiments performed. Efforts have been made to ensure accuracy with respect to numbers used (e.g., amounts, temperature, etc.) but some experimental errors and deviations should be accounted for. It should be understood that variations in the methods as described may be made without changing the fundamental aspects that the experiments are meant to illustrate.

Those skilled in the art can devise many modifications and other embodiments within the scope and spirit of the present disclosure. Indeed, variations in the materials, methods, drawings, experiments, examples, and embodiments described may be made by skilled artisans without changing the fundamental aspects of the present disclosure. Any of the disclosed embodiments can be used in combination with any other disclosed embodiment.

In some instances, some concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A fluidic device for bioassay comprising:
   a substrate with a first surface and a second surface; said substrate having a fluidic chamber formed on the first surface; wherein the fluidic chamber comprises:
   a sample chamber in fluid communication with an air valve;
   a bioassay channel having a first end in fluid communication with the sample chamber and a second end in fluid communication with a first outlet chamber, said bioassay channel comprising a first and opposing second linear array of pillars formed proximal to each of a first lateral wall and opposing second lateral wall of the bioassay channel; and
   a plurality of ports formed through the substrate from the second surface comprising:
   a first fluidic device port providing external fluid communication to the air valve;
   a second fluidic device port providing external fluid communication to the sample chamber; and
   a third fluidic device port providing external fluid communication to the first outlet chamber.

2. The fluidic device of claim 1, further comprising a processing chamber positioned between the sample chamber and the bioassay channel.

3. The fluidic device of claim 2, wherein the processing chamber is a chamber adapted to remove the chorion of a zebrafish embryo.

4. The fluidic device of claim 1, wherein the sample chamber is adapted to receive a zebrafish embryo.

5. The fluidic device of claim 1, wherein the first and opposing second linear array of pillars are configured to position a zebrafish embryo or larva for analysis.

6. The fluidic device of claim 1, wherein the bioassay channel comprises a first bioassay region in fluid communication with the sample chamber and a second bioassay region in fluid communication with the first outlet chamber, and wherein the first and opposing second linear array of pillars are configured to define the first and the second bioassay regions of the bioassay channel.

7. The fluidic device of claim 6, wherein the first bioassay region of the bioassay channel is configured to position a zebrafish embryo or larva during early-stage development.

8. The fluidic device of claim 6, wherein the second bioassay region of the bioassay channel is configured to position a zebrafish embryo or larva during late-stage development.

9. The fluidic device of claim 1, wherein the substrate comprises an optically transmissive polymer.

10. The fluidic device of claim 9, wherein the substrate comprises polydimethoxysilane.

11. The fluidic device of claim 1, wherein the fluidic device further comprises a cover plate comprising an optically transmissive material.

12. The fluidic device of claim 11, wherein the cover plate comprises glass.

13. The fluidic device of claim 1, further comprising a sample loading manifold device for loading the fluidic device, wherein the sample loading manifold device comprises a sample loading channel with an inlet end and an outlet end, and wherein the sample loading channel comprises:
   a loading chamber proximal the inlet end of the sample loading channel; and
   at least one sample loading structure in fluid communication with the loading chamber, wherein the at least one sample loading structure comprises:
   a sample trap in fluid communication with the sample loading channel; and
   a sample channel bypass loop in fluid communication with the sample trap and the sample loading channel, wherein when the sample trap is loaded with a zebrafish embryo, fluid flow through the sample loading channel is maintained through the sample channel bypass loop.

14. The fluidic device of claim 13, wherein the sample loading manifold device is positioned over the second surface of the fluidic device such that the sample trap is aligned over the sample chamber.

15. The fluidic device of claim 13, wherein the sample trap has dimensions that permit only one zebrafish embryo to be positioned within the sample trap.

16. The fluidic device of claim 15, wherein the sample trap is 1.5 mm+/−0.15 mm in its largest dimension.

17. The fluidic device of claim 15, wherein the sample channel bypass channel loop is 1.25 mm+/−0.10 mm.

18. The fluidic device of claim 1, further comprising a reagent delivery manifold device for delivering reagent to the fluidic device, wherein said reagent delivery manifold device comprises a reagent chamber having a reagent chamber inlet port and a reagent chamber outlet port, and wherein the reagent delivery manifold device is positioned over the second surface of the fluidic device such that the reagent chamber is aligned over at least one sample chamber of the fluidic device.

* * * * *